United States Patent
Si et al.

(10) Patent No.: US 8,951,734 B2
(45) Date of Patent: Feb. 10, 2015

(54) PRION-LIKE FORM OF CPEB AND RELATED COMPOSITIONS AND METHODS

(75) Inventors: Kausik Si, Kansas City, MO (US); Eric Kandel, Riverdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 2078 days.

(21) Appl. No.: 10/578,203

(22) PCT Filed: Nov. 5, 2004

(86) PCT No.: PCT/US2004/036781
§ 371 (c)(1),
(2), (4) Date: Mar. 21, 2007

(87) PCT Pub. No.: WO2005/047306
PCT Pub. Date: May 26, 2005

(65) Prior Publication Data
US 2007/0259341 A1    Nov. 8, 2007

Related U.S. Application Data

(60) Provisional application No. 60/518,385, filed on Nov. 7, 2003.

(51) Int. Cl.
| | | |
|---|---|---|
| *C12Q 1/00* | (2006.01) | |
| *C12Q 1/02* | (2006.01) | |
| *C12Q 1/68* | (2006.01) | |
| *C07K 14/435* | (2006.01) | |
| *C07K 14/47* | (2006.01) | |

(52) U.S. Cl.
CPC ........ *C12Q 1/6897* (2013.01); *C07K 14/43504* (2013.01); *C07K 14/4702* (2013.01); *G01N 2333/395* (2013.01)
USPC ................................. 435/6.13; 435/29; 435/4

(58) Field of Classification Search
None
See application file for complete search history.

(56) References Cited

U.S. PATENT DOCUMENTS

2013/0059757 A1 * 3/2013 Gitler ............................. 506/10

OTHER PUBLICATIONS

Nambu et al. Egg-laying hormone genes of Alysia: Evolution of the ELH gene family. The Journal of Neuroscience, vol. 6, No. 7, pp. 2026-2036, Jul. 1996.*
Richter, JD. CPEB: a life in translation. Trends in Biochemical Sciences, vol. 32, No. 6, pp. 279-285, May 2007.*
Kurihara et al. CPEB2, A novel putative translational regulator in mouse haploid germ cells. Biology of Reproduction, vol. 69, pp. 261-268, Apr. 2003.*
Huang et al. CPEB3 and CPEB4 in neurons: analysis of RNA-binding specificity and translational control of AMPA receptor in GluR2 mRNA. The EMBO Journal, vol. 25, pp. 4865-4876, Oct. 2006.*
Peng et al. A novel role of CPEB3 in regulating EGFR gene transcription via association with Stat5b in neurons. Nucleic Acids Research, vol. 38, No. 21, pp. 7446-7457, Jul. 2010.*
Majumdar et al. Critical role of amyloid-like oligomers of *Drosophila* Orb2 in the presistence of memory. Cell, vol. 148, pp. 515-529, Feb. 2012.*
UniGene entry Hs.131683 for *Homo sapiens* (human) CPEB3, http:www.ncbi.nlm.nih.gov/UniGene/clust.cgi?ORG=Hs &CID=131683, printed as pp. 1/3-3/3 on Feb. 18, 2014.*
International Search Report issued by the International Searching Authority (ISA/US) on Aug. 18, 2005 in connection with International Application No. PCT/US2004/036781.
Kausik S, Lindquist S and Kandel E. A Neuronal Isoform of the Aplysia CPEB Has Prion-Like Properties. Cell, Dec. 2003, vol. 115, No. 7, pp. 879-891.
Liu J and Schwartz J. The Cytoplasmic Polydenylation Element Binding Protein and Polydenylation of Messenger RNA in Aplysia Neurons. Brain Research, Jan. 2003, vol. 959, No. 1, pp. 68-76.
Darnell, R.B. Memory, Synaptic Translation, and . . . Prions? Cell, Dec. 2003, vol. 115, No. 7, pp. 767-768.
Culp, P.A., Musci, T.J. C-mos and cdc2 Cooperate in the Translational Activation of Fibroblast Growth Factor Receptor-1 during *Xenopus* Oocyte Maturation, Molecular Biology of the Cell, Nov. 1999, vol. 10, pp. 3567-3581.
Written Opinion of the International Searching Authority issued by the International Searching Authority (ISA/US) on Aug. 18, 2005 in connection with International Application No. PCT/US2004/036781.
International Preliminary Report on Patentability issued by the International Bureau of WIPO on May 8, 2006 in connection with PCT/US2004/36781.

* cited by examiner

*Primary Examiner* — Jennifer Dunston
(74) *Attorney, Agent, or Firm* — John P. White; Cooper & Dunham LLP

(57) ABSTRACT

The present invention provides methods for determining whether an agent facilitates the conversion of a cytoplasmic polyadenylation element binding (CPEB) protein from its non-prion form to its prion form. This invention also provides methods for determining the presence and amount of the prion form of CPEB protein in a cell. This invention also provides methods for facilitating the conversion of a non-prion CPEB protein to its prion form. This invention also provides an isolated prion form cytoplasmic polyadenylation element binding (CPEB) protein and compositions comprising a therapeutically effective amount of an agent that facilitates the conversion of CPEB protein from its non-prion form to its prion form, and methods of making such compositions.

15 Claims, 15 Drawing Sheets

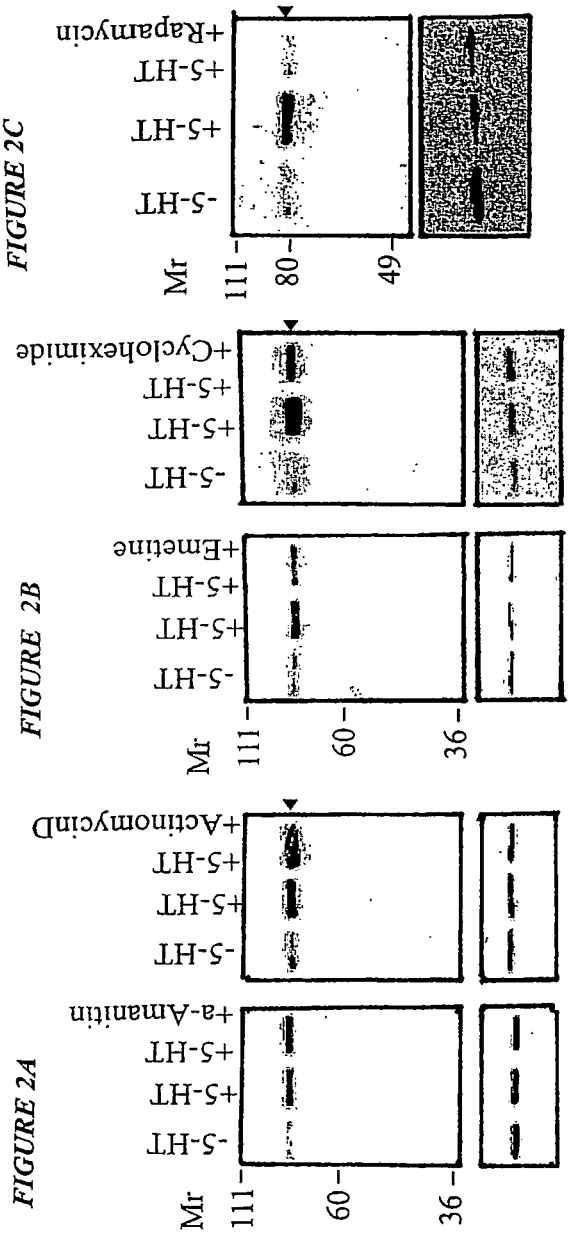

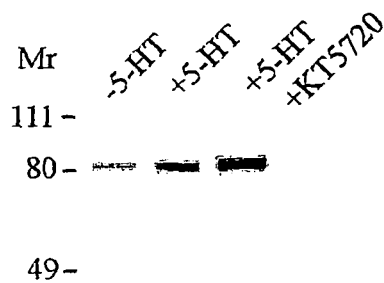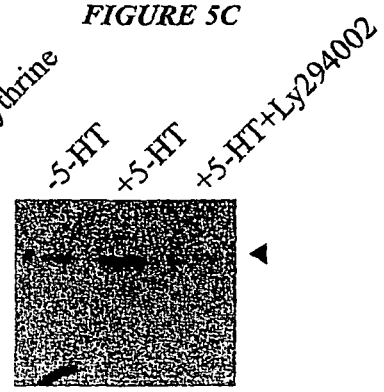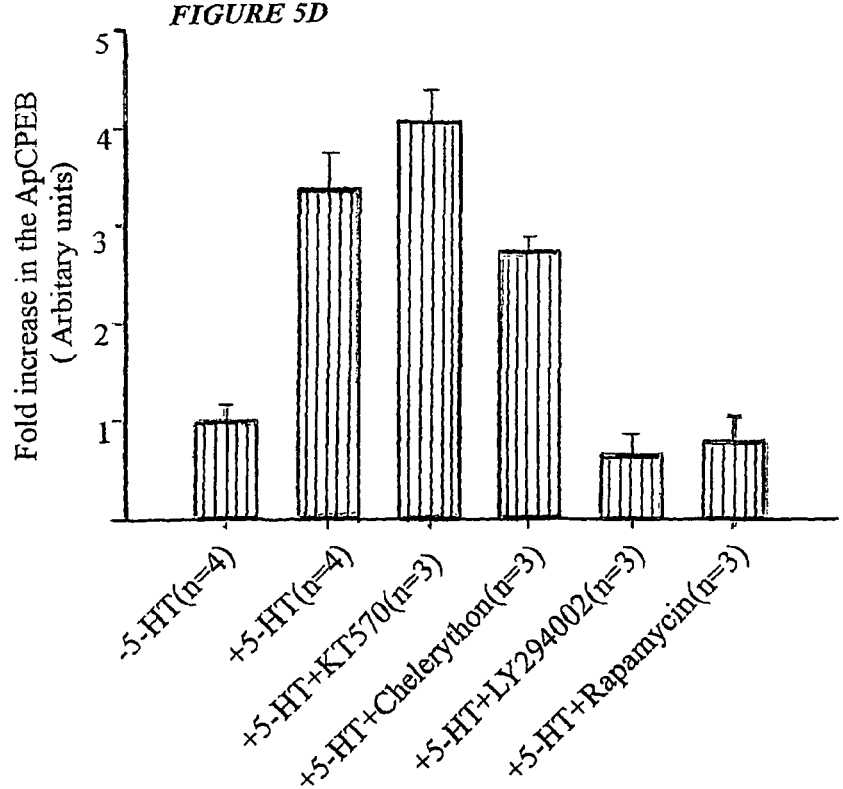

Aplysia CPEB (1-160)

MQAMAVASQS PQTVDQAISV KTDYEDNQQB HIPSNFEIFR RINALLDNSL BAMNVSCSQS QSQQQQQQTQ QQQQQQQQQQ ~48% Q/N QQQHLQQVQQ QRLLKQQQQQ AQRQQIQQQL LQQQQQKQQL QQQQQQBQLQ QQQLQLQQQL QQQLQHIQKB PSSHTYTPGP

Anti-CPEB

 FIGURE 13A — Wildtype
 FIGURE 13B — Hsp104 Overexpression
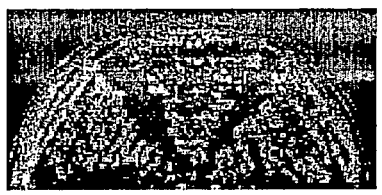 FIGURE 13C — Hsp104 Deletion
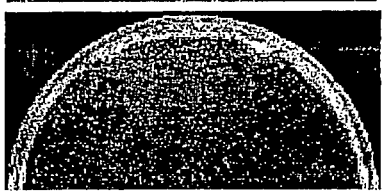 FIGURE 13D — Hsp104 overexpression in Hsp104 deletion background

US 8,951,734 B2

PRION-LIKE FORM OF CPEB AND RELATED COMPOSITIONS AND METHODS

This application is a U.S. National Stage Application under 35 U.S.C. §371 of International Application No. PCT/US2004/036781, filed Nov. 5, 2004. International Application No. PCT/US2004/036781 claims the benefit of U.S. Ser. No. 60/518,385, filed on Nov. 7, 2003, the contents of which are hereby incorporated by reference.

Throughout this application, various publications are referenced by author and publication date. Full citations for these publications may be found at the end of the specification immediately preceding the claims. The disclosures of these publications are hereby incorporated by reference into this application to describe more fully the art to which this invention pertains.

REFERENCE TO A SEQUENCE LISTING

This application incorporates-by-reference nucleotide and/or amino acid sequences which are present in the file named "120305_0575_68103_PCT_US_Sequence_Listing_SVB.txt," which is 9.40 kilobytes in size, and which was created Mar. 2, 2012 in the IBM-PC machine format, having an operating system compatibility with MS-Windows, which is contained in the text file filed Mar. 5, 2012 as part of this application.

BACKGROUND OF THE INVENTION

Prions and CPEB

The term "prion" was first applied to the proteinacious infectious agent in a group of mammalian neurodegenerative disorders, transmissible spongiform encephalopathies (Prusiner, S. B. 1998). Transmissibility is widely believed to stem from the ability of the prion form of the protein to promote a conformational change of the normal cellular protein to the prion form. A prion-like mechanism has been suggested to explain the unusual dominant, cytoplasmic inheritance of certain traits in the yeast *Saccharomyces cerevisiae* (Wickner R. B. 1994) and an array of genetic and biochemical evidence supports this hypothesis (Patino et al. 1996; Glover et al. 1997; Wickner et al. 1996; Paushkin et al. 1997; and Sparrer et al. 2000).

Unlike the mammalian prion protein, PrP, yeast prions are generally not pathogenic. Rather, they produce changes in phenotype that mimic conventional loss-of-function mutations. The faithful non-nuclear inheritance of these phenotypes results from two factors: (1) the ability of proteins in the prion conformation to promote conversion of other proteins of the same type to the prion state; and (2) transfer of the prion form of the protein from the cell's cytoplasm to its daughter cells and mating partners.

The study of fungal proteins established that stable self-perpetuating conformational changes in proteins can occur in diverse organisms, produce distinct phenotypes, involve molecules with very different physiological functions, and can sometimes be beneficial (True and Lindquist 2000).

In the well-characterized yeast prions [SUP35], [URE3], and [RNQ1], a specific region of each protein is responsible for the prion behavior (Masison et al. 1995; King et al. 1997; Sondheimer et al. 2000; DePace et al. 1998). These regions of 65-250 amino acids show no sequence homology but share four striking characteristics: (1) they are unusually rich in the polar amino acids glutamine (Q) and asparagine (N); (2) they score as having a low propensity for any particular secondary structure by structural-prediction algorithms, an indication of conformational flexibility that likely relates to the ability to switch conformational states; (3) they can exist as a soluble species or an ordered self-perpetuating aggregate; and (4) they are dispensable for the normal function of the associated protein (Tuite, M. F. 2000).

CPEB was initially identified in *Xenopus* oocytes as a translational regulator that activates dormant mRNAs by elongating their poly(A) tails (McGrew et al, 1989). CPEB serves not only as an activator, but in some cases also as a repressor. In *Xenopus* oocytes, these dual functions are controlled by phosphorylation (Mendez et al. 2002).

Neuronal CPEB Acts as a Synaptic Mark

In the brain, cell to cell communication takes place principally at synapses. Synaptic transmission encodes information in the brain. It is therefore anticipated that the ability of the synapse to use stable modifications to remember its excitatory history forms the basis of memory.

The ability of a neural cell to alter its physiochemical and electrochemical properties at the synapse in response to an external stimulus is referred to as synaptic plasticity. One form of synaptic plasticity is a long-lasting increase in synaptic strength following robust synaptic activity. This is referred to as long-term potentiation, or LTP. In the model organism, *Aplysia*, the form of synaptic plasticity that corresponds to the LTP of the mammalian hippocampus is called long-term facilitation, or LTF. LTF is induced experimentally by the application of five spaced pulses of serotonin, a neurotransmitter released by interneurons activated during learning. The five pulses are designed to stimulate the spaced training that leads to long-term memory.

Like behavioral memory, synaptic plasticity has at least two temporally distinct forms: a short-term form lasting minutes and a long-term form lasting days and weeks. Each of these forms has distinct molecular requirements. The short-term form depends on covalent modifications of pre-existing proteins and the strengthening of pre-existing synaptic connections. The long-term form requires the synthesis of new protein and the establishment of new synaptic connections.

The requirement for new protein synthesis in the long-term form of synaptic plasticity requires transcription and therefore the nucleus. Since a given neuronal cell may have many different synapses, located at some distance from the nucleus, the requirement for transcription raises the question of whether all long-term changes must necessarily be cell-wide or whether they can also be restricted to some synapses and not others.

This question was addressed using an *Aplasia* sensory-motor neuron cell culture system (Martin et al. 1997). In this system, a single bifurcated sensory neuron is plated in contact with two spatially separated motor neurons.

Application of a single pulse of serotonin (5-HT) to one of the two sets of synapses results in a synapse-specific short-term facilitation of pre-existing connections that lasts for minutes. In contrast, application of five pulses of 5-HT, designed to simulate the spaced training that leads to long-term memory, elicits a long-term facilitation (LTF) that lasts for three or more days. Whereas the short-term form does not require new protein synthesis, the long-term form requires both CREB-dependent transcription and local protein synthesis at activated synapses, leading to the stabilization of new connections. Moreover, the synapse specific long-term facilitation, initiated in one branch can be captured at the other by application of a single pulse of 5-HT (which by itself is capable of producing only a short-term facilitation). Similar observations have been made on synaptic capture in slices of mammalian hippocampus (Barco et al., 2002; Frey and Morris, 1997). Interestingly, local protein synthesis is not needed for capture per se, but it is required for the stable maintenance of the synaptic growth initiated by capture beyond 24 h (Casadio et al., 1999). Thus, the synaptic changes associated with long-term facilitation, and by implication, LTP in mammals, can be produced and maintained locally at a particular synapse.

One mechanism that has been proposed for both generating the signal from the synapse to the nucleus and for the stable insertion of new proteins at the activated synapses is local translation of mRNAs (Wells et al. 2000, Shuman et al. 1999). The general hypothesis is that mRNAs located in the dendrite are translationally dormant until synaptic activity pushes them into a translationally active state. The protein products of this translation could act synaptically, or as has been demonstrated in *Aplysia*, the proteins could act in transmitting a signal back to the nucleus (Martin et al. 1997, Casadio et al. 1999).

It is likely that the signal which induces a long-term synapse specific facilitation must both send a signal from the synapse to the nucleus that activates transcription and also mark the activated synapse. The newly synthesized mRNAs and proteins necessary for LTF are then either selectively transported to or transported globally, but selectively utilized by the marked synapse. The capturing of the synapse-specific LTF initiated in one branch by the other branch suggests a global distribution and selective utilization at the marked synapse. Synaptic capture by a single pulse of serotonin also suggests that the signaling required for short-term facilitation can produce the mark.

The synaptic mark has at least two components (Casadio et al. 1999) First, a PKA-dependent component needed for the initial capture of synapse specific facilitation and for the growth of new synaptic connections. Second, a rapamycin-sensitive, local protein synthesis-dependent component needed for the long-term maintenance of facilitation and stabilization of growth beyond 24 hrs. Since mRNAs are made in the cell body, the need for the local translation of some mRNAs suggests that these mRNAs may be dormant before they reach the site of translation. If that is true, then the synaptic mark for stabilization might be a regulator of translation capable of activating translationally dormant mRNAs.

One model for the activation of translationally dormant mRNAs in an experience-dependent fashion is cytoplasmic polyadenylation. In this model, a synaptically localized mRNA binding protein, such as CPEB, is activated by a signal at the synapse. CPEB then catalyzes the polyadenylation of specific mRNAs, which in turn promotes their local translation. CPEB is present in cultured hippocampal neurons and in the post-synaptic density fraction of a mouse synaptosomal preparation (Huang et al., 2002; Wu et al., 1998).

This polyadenylation-dependent translational control requires two cis-acting elements at the 3'UTR of the mRNAs, (1) a polyadenylation sequence AAUAAA, and (2) a cytoplasmic polyadenylation element (CPE) with a general structure of UUUUUAU (Fox et al. 1989). Regulation is through a CPE binding protein, such as CPEB (Gebauer and Richter, 1996; Hake and Richter, 1994).

CPEB has four important features which makes it an attractive candidate as a synapse-specific mark for stabilization: (1) it is activated through an extracellular signal; (2) it activates mRNAs that are translationally dormant (Schroeder et al., 1999; Stebbins-Boaz et al., 1996); (3) its localization can be spatially restricted (Bally-Cuif et al., 1998; Schroeder et al., 1999; Tan et al., 2001); and (4) a number of mRNAs targeted by CPEB are involved in cellular growth (Chang et al., 2001; Groisman et al., 2002).

SUMMARY OF THE INVENTION

The present invention provides a method for determining whether an agent facilitates the conversion of a cytoplasmic polyadenylation element binding (CPEB) protein from its non-prion form to its prion form comprising the steps of (a) contacting a population of cells with the agent, each of which cells comprises (i) an expressible nucleic acid comprising a sequence encoding a reporter protein that is translationally repressed by a cytoplasmic polyadenylation element (CPE) and (ii) a CPEB protein in its nonprion form; and (b) after a suitable period of time, determining whether the amount of reporter protein expressed in the presence of the agent is greater than the amount of reporter protein expressed in the absence of the agent, whereby greater reporter protein expression in the presence of the agent indicates that the agent facilitates the conversion of a CPEB protein from its non-prion form to its prion form.

The present invention also provides a method for determining whether an agent facilitates the conversion of a cytoplasmic polyadenylation element binding (CPEB) protein from its prion form to its non-prion form comprising the steps of (a) contacting a population of cells with the agent, each of which cells comprises (i) a nucleic acid comprising a sequence encoding a reporter protein under the negative translational control of a cytoplasmic polyadenylation element (CPE) and (ii) a CPEB protein in its prion form; and (b) after a suitable period of time, determining whether the amount of reporter protein expressed in the presence of the agent is lower than the amount of reporter protein expressed in the absence of the agent, wherein lower reporter protein expression in the presence of the agent indicates that the agent facilitates the conversion of a CPEB protein from its prion form to its non-prion form.

The present invention further provides a method for determining whether an agent facilitates the conversion of a cytoplasmic polyadenylation element binding (CPEB) protein from its non-prion form to its prion form comprising the steps of (a) contacting a population of CPEB protein with the agent, wherein a predetermined portion of the CPEB protein population is in its non-prion form; and (b) after a suitable period of time, determining whether the portion of the CPEB protein population in its prion form is greater in the presence of the agent than in the absence of the agent, whereby a greater portion of CPEB protein in its prion form in the presence of the agent indicates that the agent facilitates the conversion of CPEB protein from its non-prion form to its prion form.

The present invention also provides a method for determining whether an agent facilitates the conversion of a cytoplasmic polyadenylation element binding (CPEB) protein from its prion form to its non-prion form comprising the steps of (a) contacting a population of CPEB protein with the agent, wherein a predetermined portion of the CPEB protein population is in its prion form; and (b) after a suitable period of time, determining whether the portion of the CPEB protein population in its non-prion form is greater in the presence of the agent than in the absence of the agent, whereby a greater percentage of CPEB protein in its non-prion form in the presence of the agent indicates that the agent facilitates the conversion of CPEB protein from its prion form to its non-prion form.

The present invention also provides a method for determining the amount of the prion form of cytoplasmic polyadenylation element binding (CPEB) protein in a cell comprising the steps of (a) introducing into the cell an expressible nucleic acid comprising a sequence encoding a reporter protein that is translationally repressed by a cytoplasmic polyadenylation element (CPE); (b) determining the amount of reporter protein expressed in the cell; and (c) comparing the amount of reporter protein determined in step (b) with the amount of reporter protein expressed in a cell having therein a known amount of the prion form of CPEB protein, so as to thereby determine the amount of prion form of CPEB protein in the cell.

The present invention also provides a method for determining whether the prion form cytoplasmic polyadenylation element binding (CPEB) protein is present in a cell comprising the steps of (a) introducing into the cell an expressible nucleic acid comprising a sequence encoding a reporter protein that is translationally repressed by a cytoplasmic polyadenylation element (CPE); and (b) determining whether the reporter protein is expressed in the cell, wherein the expression of the reporter protein indicates that the prion form of CPEB protein is present in the cell.

The present invention also provides a method for facilitating the conversion of a non-prion cytoplasmic polyadenylation element binding (CPEB) protein to its prion form comprising contacting the CPEB protein with a CPEB protein in its prion form.

The present invention also provides a method for facilitating the conversion of a non-prion cytoplasmic polyadenylation element binding (CPEB) protein into its prion form comprising contacting the CPEB protein with an agent that facilitates the conversion of non-prion CPEB to its prion form.

The present invention also provides an isolated prion form cytoplasmic polyadenylation element binding (CPEB) protein.

The present invention also provides a composition comprising a therapeutically effective amount of an agent that facilitates the conversion of a cytoplasmic polyadenylation element binding (CPEB) protein from its non-prion form to its prion form, and a pharmaceutically acceptable carrier.

The present invention also provides a composition comprising a therapeutically effective amount of an agent that facilitates the conversion of a cytoplasmic polyadenylation element binding (CPEB) protein from its prion form to its non-prion form, and a pharmaceutically acceptable carrier.

Finally, the present invention provides a method for making a composition comprising the steps of (a) identifying an agent that facilitates the conversion of a cytoplasmic polyadenylation element binding (CPEB) protein from its prion form to its non-prion form according and (b) admixing the agent identified in step (a) with a pharmaceutically acceptable carrier.

BRIEF DESCRIPTION OF THE FIGURES

FIG. 2: *Aplysia* CPEB is induced postranscriptionally. Total protein extracts from *Aplysia* pleural ganglia (8 ug of protein) were blotted with ApCPEB77 antibodies following treatment with (A) transcription inhibitors, (B) protein synthesis inhibitors, (C) rapamycin. The membranes were stained with Gold stain and gold stained band is shown as loading control for actinomycin D, alpha-amanitin, and emetine. The same membrane was probed with either anti-synaptophysin (for cycloheximide exp) or anti-*Aplysia* ubiquitin hydrolase (for rapamycin exp) as controls for equal loading of the gel.

FIG. 5: ApCPEB induction is sensitive to PI3 kinase inhibitor: *Aplysia* Pleural ganglia was treated for 30 min with PKA inhibitor KT5720 (a), PKC inhibitor Chelerythrine (b) or PI3 kinase inhibitor LY294002 (c) before stimulation with 5-HT for an hour. Fold induction of ApCPEB is shown in (d). The western blots were scanned and quantified using NIH image. Each set of pharmacological inhibitors had an independent untreated and treated controls. The average fold induction is 3.3±0.4.

FIG. 11C: Right panel: Western blotting of the pooled 300 mM fractions of the SOURCE S cation exchanger with Anti *Aplysia* CPEB antibodies.

FIG. 13: Hsp104 influence the activity state of *Aplysia* CPEB. W303a (a, b) or W303aΔhsp104 (A3224) (c, d) were transformed with ApCPEB and β-gal-CPE construct. The Leu+Ura+ cells were replica plated on x-gal plates. The resulting blue colonies were transformed with an Hsp104 overexpressing plasmid (5312) with HIS3 marker (b, d). The His+Leu+Ura+ cells were replica plated on X-gal containing plates. Overexpression of Hsp104 cures the blue phenotype (b).

DETAILED DESCRIPTION OF THE INVENTION

Figure 1A:
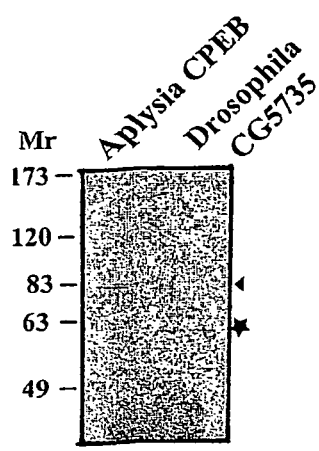
FIG. 1A: ApCPEB cDNA and *Drosophila* CG5735RA cDNA were translated in vitro in rabbit reticulocyte lysates supplemented with [35S]methionine, separated on a 10% SDS-PAGE gel and autoradiographed. The cDNA produced 82 kd (*Aplysia* ◄) and 62 kd (*Drosophila**) proteins.

The present invention provides a method for determining whether an agent facilitates the conversion of a cytoplasmic polyadenylation element binding (CPEB) protein from its non-prion form to its prion form comprising the steps of (a) contacting a population of cells with the agent, each of which cells comprises (i) an expressible nucleic acid comprising a sequence encoding a reporter protein that is translationally repressed by a cytoplasmic polyadenylation element (CPE) and (ii) a CPEB protein in its nonprion form; and (b) after a suitable period of time, determining whether the amount of reporter protein expressed in the presence of the agent is greater than the amount of reporter protein expressed in the absence of the agent, whereby greater reporter protein expression in the presence of the agent indicates that the agent facilitates the conversion of a CPEB protein from its non-prion form to its prion form.

The present invention also provides a method for determining whether an agent facilitates the conversion of a cytoplasmic polyadenylation element binding (CPEB) protein from its prion form to its non-prion form comprising the steps of (a) contacting a population of cells with the agent, each of which cells comprises (i) a nucleic acid comprising a sequence encoding a reporter protein under the negative translational control of a cytoplasmic polyadenylation element (CPE) and (ii) a CPEB protein in its prion form; and (b) after a suitable period of time, determining whether the amount of reporter protein expressed in the presence of the agent is lower than the amount of reporter protein expressed in the absence of the agent, wherein lower reporter protein expression in the presence of the agent indicates that the agent facilitates the conversion of a CPEB protein from its prion form to its non-prion form.

In an embodiment of either of the preceding two methods, the CPE comprises the sequence: 5'GGAATTCGGCACCAT-GTGCTTCTGTAAATAGTGTATTGT-GTTTTTAATGTTGG ACTGGTTGGAATAAAGCTCTA-GAGC-3' (SEQ ID NO:1).

In another embodiment, the cell is a eukaryotic cell. In a further embodiment, the eukaryotic cell is a yeast cell. In a further embodiment, the yeast cell is an *S. cerevisiae* cell. In a preferred embodiment, the cell is a yeast cell and the reporter protein is β-galactosidase. In a further embodiment, the amount of β-galactosidase is determined by determining, in the presence of a chromogenic substrate for β-galactosidase, the intensity of color due to β-galactosidase activity within the population of cells. In one embodiment, the chromogenic substrate is 5-bromo-4-chloro-3-indolyl β-D-galactopyranoside.

In one embodiment of either of the preceding two methods, the CPEB protein is endogenously expressed in the population of cells. In a further embodiment, the population of cells is obtained from central nervous system tissue. In a preferred embodiment, the population of cells is a population of neuronal cells. In one embodiment, the population of cells is further contacted with a neurotransmitter prior to, concurrently with, or subsequent to contacting with the agent. In an embodiment of the first method, the neurotransmitter is serotonin.

As used herein, the "prion" form of CPEB protein shall mean the form of CPEB protein which exists in a self-perpetuating and active state. The "non-prion" form of CPEB protein shall mean the form of CPEB protein which, although having the same amino acid sequence as the prion form, exists in a non-self-perpetuating and non-active state.

As used herein, a "suitable period of time" before measuring protein expression in the instant methods means any time which would permit protein expression in the absence of an agent that inhibits protein expression. In one embodiment, a suitable period of time is at least 10 minutes. In other embodiments, a suitable period of time is at least 30 minutes, one hour, 3 hours, 12 hours, one day, or two days.

The present invention further provides a method for determining whether an agent facilitates the conversion of a cytoplasmic polyadenylation element binding (CPEB) protein from its non-prion form to its prion form comprising the steps of (a) contacting a population of CPEB protein with the agent, wherein a predetermined portion of the CPEB protein population is in its non-prion form; and (b) after a suitable period of time, determining whether the portion of the CPEB protein population in its prion form is greater in the presence of the agent than in the absence of the agent, whereby a greater portion of CPEB protein in its prion form in the presence of the agent indicates that the agent facilitates the conversion of CPEB protein from its non-prion form to its prion form.

The present invention also provides a method for determining whether an agent facilitates the conversion of a cytoplasmic polyadenylation element binding (CPEB) protein from its prion form to its non-prion form comprising the steps of (a) contacting a population of CPEB protein with the agent, wherein a predetermined portion of the CPEB protein population is in its prion form; and (b) after a suitable period of time, determining whether the portion of the CPEB protein population in its non-prion form is greater in the presence of the agent than in the absence of the agent, whereby a greater percentage of CPEB protein in its non-prion form in the presence of the agent indicates that the agent facilitates the conversion of CPEB protein from its prion form to its non-prion form.

In an embodiment of these methods, determining the portion of the CPEB protein population in its prion or non-prion form comprises determining the susceptibility of the CPEB protein to protease digestion. In another embodiment, determining the portion of the CPEB protein population in its prion or non-prion form comprises determining the amount of CPEB protein aggregate collectable by centrifugation. In a further embodiment, determining the portion of the CPEB protein population in its prion or non-prion form comprises determining the ability of CPEB protein to increase the expression of a protein that is translationally repressed by a CPE.

The present invention also provides a method for determining the amount of the prion form of cytoplasmic polyadenylation element binding (CPEB) protein in a cell comprising the steps of (a) introducing into the cell an expressible nucleic acid comprising a sequence encoding a reporter protein that is translationally repressed by a cytoplasmic polyadenylation element (CPE); (b) determining the amount of reporter protein expressed in the cell; and (c) comparing the amount of reporter protein determined in step (b) with the amount of reporter protein expressed in a cell having therein a known amount of the prion form of CPEB protein, so as to thereby determine the amount of prion form of CPEB protein in the cell.

The present invention also provides a method for determining whether the prion form cytoplasmic polyadenylation element binding (CPEB) protein is present in a cell comprising the steps of (a) introducing into the cell an expressible nucleic acid comprising a sequence encoding a reporter protein that is translationally repressed by a cytoplasmic polyadenylation element (CPE); and (b) determining whether the reporter protein is expressed in the cell, wherein the expression of the reporter protein indicates that the prion form of CPEB protein is present in the cell.

The present invention also provides a method for facilitating the conversion of a non-prion cytoplasmic polyadenylation element binding (CPEB) protein to its prion form comprising contacting the CPEB protein with a CPEB protein in its prion form.

The present invention also provides a method for facilitating the conversion of a non-prion cytoplasmic polyadenylation element binding (CPEB) protein into its prion form comprising contacting the CPEB protein with an agent that facilitates the conversion of non-prion CPEB to its prion form.

The present invention also provides an isolated prion form cytoplasmic polyadenylation element binding (CPEB) protein. In one embodiment, the protein is isolated from a eukaryotic cell. In a further embodiment, the protein is an *Aplysia* CPEB protein, mouse CPEB protein, or human CPEB protein.

The present invention also provides a composition comprising a therapeutically effective amount of an agent that facilitates the conversion of a cytoplasmic polyadenylation element binding (CPEB) protein from its non-prion form to its prion form, and a pharmaceutically acceptable carrier.

The present invention also provides a composition comprising a therapeutically effective amount of an agent that facilitates the conversion of a cytoplasmic polyadenylation element binding (CPEB) protein from its prion form to its non-prion form, and a pharmaceutically acceptable carrier.

Finally, the present invention provides a method for making a composition comprising the steps of (a) identifying an agent that facilitates the conversion of a cytoplasmic polyadenylation element binding (CPEB) protein from its prion form to its non-prion form according and (b) admixing the agent identified in step (a) with a pharmaceutically acceptable carrier.

This invention will be better understood from the Experimental Details that follow. However, one skilled in the art will readily appreciate that the specific methods and results discussed are merely illustrative of the invention as described more fully in the claims which follow thereafter.

Experimental Details

Characterization of *Aplysia* CPEB

CPEB has four important features which make it an attractive candidate as a synapse-specific mark in long-term changes in synaptic plasticity: (1) it is activated through an extracellular signal; (2) it activates mRNAs that are translationally dormant; (3) its localization can be spatially restricted; and (4) a number of mRNAs targeted by CPEB are involved in cellular growth.

The following describes a neuron-specific isoform of CPEB in *Aplysia*, ApCPEB. Functional characterization of ApCPEB demonstrates that it is induced in the neurites of sensory neurons by a single pulse of serotonin. This induction is dependent on rapamycin-sensitive protein synthesis, indicating a requirement for translation. Furthermore, a depletion of ApCPEB locally at the activated synapse inhibits the long-term maintenance of synaptic facilitation but not its early expression at 24 hrs. Thus, ApCPEB has the properties required of the local protein synthesis-dependent component of marking. These results further support the idea that there are separate mechanisms for initiation of the long-term process and its stabilization. We have a found a similar isoform of CPEB in *Drosophila*, mouse and human nervous system. Hence, the mechanism seems to be evolutionary conserved.

Methods

Cloning of *Aplysia* CPEB

Full length CPEB was cloned by degenerate PCR and 5' and 3$^r$ RACE (rapid amplification of cDNA ends). To make first strand cDNA total RNA was isolated either from *Aplysia* oocytes or pleural ganglia (as a source of sensory cells) using Trizol TRIZOL® (monophasic solution of phenol and guanidine isothiocyanate) reagent (Life Technologies). 5 ug of total RNA was reverse transcribed using Life Technologies first strand cDNA synthesis kit. For degenerate PCR cDNA prepared from *Aplysia* oocytes was amplified by Taq DNA polymerase (Roche) using 100 pMol of each primer in the PCR cycle: $94^2$C 1 min, $42^a$C 1 min, $72^2$C 1 min—30 cycles. A 500 bp cDNA fragment was cloned. Two degenerate primers CPEB1-5' GCGG-AATTCGTNSARGTNATHCCNTGG-3' (SEQ ID NO:2) and CPEB2-5' GCGGGATCCT-GNTGC-CANTSCCARCA-3' (SEQ ID NO:3) were designed from the conserved C-terminal RNA binding domain of CPEB from several other species. Using the sequence information from the 500 bp cDNA fragments, 5' and 3' Rapid Amplification of cDNA Ends (RACE) were carried out on CNS and ovatestis mRNA, (Clontech). The 5' RACE primers 5'-CACTGTCT-TGTTCGACTCCAG-3' (SEQ ID NO:4) and 5'-AACA-CATGGTTACT-GTCCGC-3' (SEQ ID NO:5) and 3' RACE primer 5'-CATGAAAGCCGTGCAAGCTGCATT-3' (SEQ ID NO: 6) were used. The protein encoded by this cDNA fragment had –80% homology to the RNA binding domain of CPEB of other species.

Cloning of *Drosophila* CG5735

PolyA mRNA's of different developmental stages of *Drosophila* were purchased from Clontech. To obtain adult head and body mRNA 50 *Drosophila* heads were manually dissected and total mRNA was prepared using the Trizol TRIZOL® method (Guanidinium thiocyanate-phenol-chloroform extraction). The first strand cDNA was made from 1

μg of PolyA mRNA or 5 ug of total mRNA. The following primer pairs were used for the PCR: CG5735RA-5' primer-CGGGATCCATGTACAACAAATTTGTTA (SEQ ID NO:7) and 3' primer-TCCCCGCGGCG-ATCCTCCGC-CTCCTC (SEQ ID NO: 8); CG5735RB-D-5' primer-ATG-GACTCGCTCAAGTTACCA (SEQ ID NO:9) and 3' primer-TCCCCGCGGCG-ATCCTCCGCCTCCTC (SEQ ID NO: 8); Orb-5' primer-CGCG-ATGCCTGATTGATTGTTGAA (SEQ ID NO:10) and 3'-primer-TGTGCGTTATTT-TATCGTTTAGTG (SEQ ID NO:11); rp49-5' primer-GACT-TCATCCGCCACCAGTCG (SEQ ID NO:12) AND 3' primer-CACCAGGAACT-TCTTGAATCCG (SEQ ID NO:13). To clone the CG5735RA open reading frame, first strand cDNA made from adult head mRNA was PCRed with the 5' primer-CGGGATCCATGTACAAC-AAATTTGTTA (SEQ ID NO:7) and 3' primer-GCCTCGAGAAGCTTT-TAACACCAGCGAAAGG-GGAC (SEQ ID NO: 14) and cloned into the BamHI/XhoI site of pRSETA (for His$_6$-tag) or into the same sties of pKS(+). For expression in TnT lysate the pKS(+)-CG573 5RA was transcribed with T3 RNA polymerase.

Cloning of *Drosophila* Homologue of the *Xenopus Rho* Family Guanine Nucleotide Exchange Factor GEF or DroGEF.

To clone DroGEF single stranded cDNA made from *Drosophila* brain mRNA was PCR amplified using 5' primer CGGGATCCATGCT-GGACAGCAACAACAG (SEQ ID NO:15) and 3' primer GACTAGTCTAGAATAGATTAG-CAAAG-AAATC (SEQ ID NO:16). The PCR product was cloned into the pCRTOPOII vector (invitrogen) and digested with BamH1. The ~1.8 kb fragment was cloned into the same site of pGEX2T and a clone in which the insert was in correct orientation was subsequently used to transform *E. coli* BL21 (DE3).

Injection of N-Actin mRNA into the Oocytes.

The neuronal actin 3'UTR was obtained by PCR using the 5' primer 5'-GGGAATTCGTCTGGAGCCACCAACAC-3' (SEQ ID NO:17) and 3' primer 5'-CGGATCCAT-TTATTAA-CATTGTATAAAAAATACAGTTGAAC-3'(SEQ ID NO:18). To mutate the CPE element, the 3'primer was changed to 5'=CGGATCCATTTATTAACA-TTGTATGG-GAAATACAGT-TGAAC-3' (SEQ ID NO:19). The N-actin 3UTR's were cloned into the pCR2.1 vector (Invitrogen). To create the Luciferase-SV403' UTR construct, pGL3-Basic (Promega) was digested with HindIII-BamHI and ligated into the same site of the vector pKSH. To make the Luciferase-Actin 3' UTR constructs, the pKSII-Luciferase-SV403UTR construct was digested with ApaI-XbaI. The Luciferase ORF was isolated and cloned into the same site of pCR2.1-Actin 3'UTR to create the Luciferase-Actin 3'UTR construct. To make $^7$Methyl Guanosine capped mRNA the pKSII-luciferase-SV40 was linearized with BamHI and transcribed with T3 RNA polymerase using mMEASGE mMACHINE MMESSAGE MMACHINE® (High Yield Capped RNA Transcription Kit) (Ambion). The pCR2.1 luciferase-Actin 3'UTR was transcribed with T7 RNA polymerase following digestion with BamHI. The mRNA was phenol-chloroform extracted, precipitated with ethanol and resuspended in nuclease free water. *X. laveis* oocytes were isolated and injected as described previously. Five oocytes were homogenized in 150 ul of luciferase cell lysis buffer (Roche). The total homogenate was centrifuged at 14,000 rpm in a micro centrifuge for 10 min and 10 ul of the clear lysates was assayed. The reaction was started by injecting 100 ul of the luciferase substrate (Roche).

2D Phosphoprotein and Western Analysis of CPEB

The 2D gel electrophoresis was carried out using JPGphor-immobilinc-d^y-atrip IPGPHOR™ (Isoelectric Focusing System) IMMOBILINE™ DRYSTRIP (gel strip containing an immobilized pH gradient) following the manufacturer's protocol (Amersham Pharmacia Biotech). In brief, the *Aplysia* pleural ganglia were desheathed and the sensory cell clusters removed in ice cold seawater. The cells were incubated in phosphate free media supplemented with 1 mCi of $^{32}$P-orthophosphate for 16 h at 17° C. The sensory cells were then treated with 10 uM 5-HT for either 10 min or 60 min and total cell extracts were prepared in 2D gel electrophoresis buffer containing phosphatase inhibitors. The total cell extracts (~10 ug of total protein) were subjected to isoelectric focusing in the first dimension on an 18 cm 4-7 immobilinc-ehey strip IMMOBILINE™ DRYSTRIP (gel strip containing an immobilized pH gradient) and then in the second dimension on a 7.5% SDS-PAGE gel. The proteins were transferred to PVDF membrane and blotted with affinity purified anti-CPEB 533 antibodies. Following western blotting the membranes were air dried, checked for residual chemiluminescence's signal and exposed to autoradiographic films for 2 days. For phosphatase treatment the cell extracts were prepared in a buffer containing 10 mM HEPES-NaOH (pH 7.6), 600. mM KCl, 3 mM MgCl$_2$, 1 mM DTT, 5% glycerol and protease inhibitors. The extracts were then incubated with alkaline or acid phosphatases for 30 min at room temperature and subsequently processed for 2D western analysis as mentioned previously. For in vitro phosphorylation analysis, *Aplysia* CPEB ORF in the pKS(+) vector was transcribed and translated in TnT lysates (Promega) using SP6 RNA polymerase either in the presence of $^{35}$S-methionine or with cold amino acids in a 50 ul reaction volume. 4 ul of the reaction-mix for unlabelled proteins and 2 ul of the reaction mix for $^{35}$S-methionine labeled protein were than incubated with 4 units of bovine catalytic subunits of protein kinase A (Sigma) and 1 uCi of [$\gamma$~$^{32}$P]ATP (3000 ci/mmol) at room temperature in 40 mM Tris-HCl (pH 7.4), 20 mM MgCl$_2$, 0.1 mM ATP and 0.1 mg/ml BSA for 30 min. The reaction mix was boiled with SDS-PAGE gel loading buffer and analyzed on a 10% SDS-PAGE gel. The gel was dried and exposed to autoradiographic film for 48 h. A biotinylated substrate for PKA (100 uM) (Promega) was also incubated with PKA and 1 uCi of [$\gamma$~$^{32}$P] ATP. After 30 min the biotinylated substrate was purified using streptavidin magnetic beads and $^{32}$P incorporation in the biotinylated substrate was measured in the scintillation counter.

In Situ Hybridization of CG5735

240 nucleotides from the N-terminus of the CG5735RA ORF were cloned into TopoII vector (Invitrogen) and transcribed with T7 or SP6 RNA polymerase (Promega) in the presence of digoxigenin RNA labeling nucleotide mix (Roche Chemicals) following the manufacturer's protocol. The DIG-labeled mRNA was precipitated with LiCl$_2$ and ethanol and washed with 70% ethanol. The mRNA was resuspended in diethyl pyrocarbonate treated water and the incorporation of DIG-labeled nucleotides into the RNA was verified by dot blotting. *Drosophila* heads were frozen in OCT and 10 micron sections were fixed in 4% paraformaldehyde in PBS for 10 min at room temperature. After fixation the slides were washed three times with PBS and treated with triethanol amine/acetic anhydride solution (0.575 gm triethanol amine, 67 μl of 10N NaOH, 75 μl of acetic anhydride in 30 ml water). The slides were then washed with PBS, permeabilized with 0.1% Triton™ X-100 and pre-hybridized at 65° C. for 2 hr in hybridization buffer (50% formamide, 5×SSC, 5×Denhardt's reagent, 250 μg/ml of yeast tRNA, 500 μg/ml of salmon sperm DNA). The DIG RNA probes were denatured at 80° C. for 5 min before they were added to the hybridization mix. The mixture was then hybridized at 65° C. for 16 to 18 hr in a humidified chamber. Following hybridization the slides were washed one time with 5×SSC at 65° C. for 10 min and three times with 0.2×SSC at 65° C. for 30 min. Slides were washed with 0.2×SSC at room temperature for 5 min and incubated with buffer B1 (lot heat inactivated horse serum in PBS) at room temperature for 1 h. They were then incubated over night in buffer B1 containing a 1:1000 dilution of mouse Anti-DIG antibodies coupled to alkaline phosphatase. Slices were washed three times with PBS at room temperature (30 min each wash) and washed once for 5 min with buffer B3 at room temperature (100 mM Tris-HCl, pH 9.5, 0.5 mM $MgCl_2$) and developed with NBT/BCIP for 24 h.

Yeast Strains, Plasmids and Cloning

The genotype of yeast strains used are: W303 (a or α; ade2-1; his3-11.15; leu2-3.12; trp1-1; ura3-1); A3464 (W303a; ade2-1; his3-11.15; leu2-3.12; trp1-1; ura3-1; can1-100, p0, kar1-Δ15); A365 (W303α; ade2-1; leu2-3.12; ura3-1; can1-100); A3224 (W303a; ade2-1; his3-11.15; leu2-3.12; trp1-1; ura3-1; can1-100, hso104:kanMX4); A3933 (W303a; ade2-1; h is 3-11.15; leu2-3.12; trp1-1; ura3-1; can 1-100; Δhsp82).

CPEBQ, consisting of the N-terminal 480 nucleotides of ApCPEB, was amplified by PCR from the full length *Aplysia* CPEB cDNA using the following primers (written 5' to 3'): 5': CGGGATCCATGCAAGCCATGGCCGT (SEQ ID NO:20); 3': TCCCCGCGGTGGACCAGGCGTGTA (SEQ ID NO:21).

CPEBQ-EGFP was prepared by cloning CPEBQ PCR product into the BamHI/SacII site of the plasmid p2HG in-frame with EGFP. CPEBQ-GR$^{526}$ was prepared by replacing the NM fragment of the plasmid pG1-NMGR526 with CPEBQ.

A yeast ApCPEB expression vector was prepared by cloning the AatII (blunt ended)/BamHI fragment of the ApCPEB open reading frame contained in pGEM7Zf(+) into the BamHI/SmaI site of the pRS316-derived vector, p9214.

pGEM-CPE, consisting of 78 nucleotides of the cyclin B1 3'UTR, was prepared by hybridizing the oligo, 5'GGAAT-TCGGCACCATGTGCTTCTGTAAATAGTG-TATTGTGTTTTAATGTTGG ACTGGTTG-GAATAAAGCTCTAGAGC-3' (SEQ ID NO:1), with its antisense oligo and cloning into the EcoRI/XbaI site of pGEM7Z(f+).

pGEM-β-gal-CPE was prepared by cloning β-gal into the HindIII/SmaI site of pGEM-CPE. The HindIII/XbaI fragment of pGEM-β-gal-CPE was then subcloned into the yeast centromeric plasmid pRS315. pRS315-β-gal-CPE was prepared by subcloning a 900 bp SacI (blunt ended)/XhoI GPD promoter fragment into the ApaI (blunt ended)/XhoI site of pRS315.

To create full-length *Aplysia* CPEB-cpGFP construct the *Aplysia* CPEB was amplified by PCR.

To overexpress yeast Hsp104, the plasmid 5312 was created by cloning the 3.5 kb Hsp104 coding region under the GPD promoter in a plasmid with HIS3 marker.

In Vitro Translation, Recombinant Protein and Antisera Production

The *Aplysia* CPEB full length cDNA was cloned into pKS (+) (Stratagene) and translated using a TnT coupled transcription-translation kit (Promega) in the presence of [$^{35}$S]methionine. Recombinant protein was prepared by cloning ApCPEB into the His tag vector pRSETA (Novagen). The resulting $His_6$-CPEB fusion protein was expressed in *E. coli* and purified using a QIAexpress™ system under denaturing conditions (Qiagen).

Two rabbit antisera were raised, one against the 17 amino acid C-terminal peptide $^{644}$LCNSHQGNYFCRDLLCF$^{660}$ (CPEB77) (SEQ ID NO:22) and one against the purified recombinant $His_6$-CPEB (533). The CPEB77 antibody was affinity purified in a peptide column (Babco).

The *Drosophila* CG5735RA cDNA was cloned by RT-PCR from adult *Drosophila* head mRNA (See supplemental material for detail) and cloned into the TOPOII Dual vector (Invitrogen) for expression in TnT lysate. To raise antibodies, CG5735RA was expressed as $His_6$ tagged protein in *E. coli* and the purified recombinant protein was injected into rabbits (Babco). The rabbit antisera was further affinity purified against the recombinant protein.

Sucrose Gradient of CPEBQ-GR:

The velocity gradient analysis was carried out essentially as described previously with the following modifications. Blue or white cells expressing CPEBQ-GR$^{526}$ were grown in selective media to an optical density at 600 nm of 1.0. Approximately 100 ml of the culture was harvested and resuspended in 500 ul of lysis buffer containing 25 mM Tris-HCl (7.5), 100 mM NaCl, 5 mM $MgCl_2$, 1 mM DTT, and 5% glycerol. Cells were broken with glass beads and centrifuged at 20,000×g for 20 min at 4° C. and the supernatant was collected. 2 ml step gradients were made using 0.5 ml of 40% sucrose in lysis buffer and 1.5 ml of 30% sucrose in lysis buffer. Approximately 1 mg of total protein (100 ul) was loaded on top of the gradient and centrifuged for 1 hr and 30 min at 45000 rpm at 4° C. in SW65i rotor. 200 ul fractions were collected from the top of the gradient and $\frac{1}{10}^{th}$ of the fraction was separated by electrophoresis on a 10% SDS-PAGE gel. The proteins were transferred to a PVDF membrane and incubated with 1:3000 dilutions of rabbit anti-GR polyclonal antibodies (Santa Cruz Biotechnology) followed by a 1:10000 dilution of anti-rabbit secondary antibody coupled to horseradish peroxidase (HRP). For the ribosomal protein Tcm1P, the blot was incubated with 1:1000 dilution of monoclonal Anti-Tcm1p antibody and developed with HRP coupled anti-mouse secondary antibody.

Purification of *Aplysia* CPEB

One liter of culture ($OD_{600}$=1) was harvested and resuspended in buffer A containing 150 mM NaCl, 50 mM HEPES (pH 7.6), 2 mM $MgCl_2$, 1 mM DTT, 5% glycerol and protease inhibitors. Cells were broken in a bead beater and centrifuged twice at 8000 rpm at 4 C in a SS34 rotor. The protein concentration of the supernatant was measured and approximately 100 mg of the protein was loaded into a 2 ml SOURCE™ 30S (1:50) column pre-equilibrated with buffer A. The column washed with 20-column volumes of the loading buffer and eluted with Buffer A plus 150 mM NaCl. 1 ml fractions were collected and $\frac{1}{20}^{th}$ of the fraction was used for detection of ApCPEB by Western analysis with ApCPEB77 antibodies. Fractions containing ApCPEB were pooled, and concentrated.

3×FLAG Purification

Total cell lysates were prepared from 200 ml of overnight culture in FLAG buffer containing 50 mM Tris-HCl (7.5), 150 mM NaCl, 1 mM EDTA, 1% Triton X-100 and protease inhibitors. Cell lysates were cleared by centrifugation and 1 mg of total protein was incubated with FLAG M2-agarose beads for 6 hrs at 4° C. The beads were washed three times with FLAG buffer and the bound material was eluted with in 150 ul of FLAG buffer containing 20 ug of FLAG peptide. 30 ul of the eluate was separated on an 8% SDS-PAGE gel and ApCPEB was detected by Western analysis using either a 1:500 dilution of affinity purified ApCPEB77 or a 1:500 dilution of the anti-FLAG polyclonal antibody.

Protease Assay

For the protease assay of CPEBQ-GR$^{526}$ 110 ul of the sucrose gradient fractions was incubated with 100 ng of freshly prepared proteinase K at room temperature (23° C.). At designated times, 20 ul of the reaction was added directly to SDS-PAGE gel loading buffer and boiled. Following electrophoresis, CPEBQ-GR$^{526}$ was detected by Western analysis using a 1:2000 dilution of rabbit anti-rat GR antibody. For the CPEB full-length assay, 100 ul (~0.5 mg/ml) of the SOURCE™ S purified fractions was incubated at RT with 75 ng of freshly prepared V8 proteinase. At designated times, 30 ul of the reaction product was added to SDS gel loading buffer and separated on a 7.5% SDS-PAGE gel. ApCPEB protein was detected by Western analysis using either a 1:500 dilution of affinity purified ApCPEb77 or a 1:3000 dilution of the 463 antibody.

Serotonin Stimulation and Western Blotting

Aplysia weighing 80-100 grams were used for serotonin (5-HT) stimulation. For whole animal stimulation, the animals were stimulated for 1-1.5 hr at 17° C. with 100 uM of freshly prepared serotonin (Sigma) and then moved to sea water at 17° C. At designated times the pleural ganglia were dissected out. The dissection was carried out in ice cold seawater and frozen in a dry ice-ethanol bath. To apply different pharmacological agents, the pleural ganglia were dissected out and rested for 3-4 hrs at 17° C. before initiation of the treatment. The pleural ganglia were stimulated with 10 uM serotonin instead of 100 uM.

For western blotting pleural ganglia were homogenized in a buffer containing 600 mM KCl, 10 mM HEPES (7.4), 3 mM $MgCl_2$, 1 mM DTT, and 0.2% NP-40; rotated at 4° C. for 20 min, centrifuged at 14,000×g for 10 min and the supernatant was collected. Approximately 10 ug of total protein was separated on a 10% SDS-PAGE gel and transferred to PVDF membrane. The membranes were blotted with affinity purified CPEB 533 (1:4000), rabbit affinity purified Aplysia Ubiquitin hydrolase (1:1500), rabbit anti-synaptophysin (Zymed) (1:3000), mouse anti-human Hsp70 (1:4000) (BD Biosciences) or monoclonal anti-tubulin (1:3000) (Sigma) followed by incubation with 1:10,000 dilution of HRP coupled anti-rabbit or anti-mouse secondary antibody (Cell signaling) and visualized by chemiluminescence (Pierce chemical). For peptide competition the CPEB77 antibody was preincubated with the peptide (1:20 w/w) at 4° C. for 30 min.

GST Pulldown

The yeast Cft1 open reading frame was fused to GST in N-terminal end and six histidine residues at the C-terminal and the resulting GST-Cft1-$H_6$ protein was purified as described previously (Dichtl et al. 2002). GST-Cft1-$H_6$, GST-FXR, and GST were bound to 50 ul of glutathione-sepharose 4B (Pharmacia) in phosphate-buffered saline containing 0.01% NP-40, 0.02% Triton™ X-100, 1 mM DTT, 5% Glycerol and protease inhibitor cocktail set 111 (Calbiochem). ApCPEB open-reading frame was transcribed and translated in the presence of 35S-methionine in TnT lysate (Promega) in a 50 ul reaction volume. For GST pull down 50 ul of the GST beads were incubated with 10 ul of the TnT lysate containing 35S-labelled protein in the presence of 0.2 mg/ml of purified BSA and 100 ug/ml of RnaseA for 1 h at 4 C. The GST beads were washed four times with PBS+ 0.01% NP40+0.02% Triton™ X-100 and the bound proteins were eluted with SDS-PAGE gel loading buffer.

To make GST-DroCG5735 the CG5735 ORF was cloned into the pGEX2T vector. The recombinant protein was purified in the glutathione sepharose 4B column under native conditions as recommended by the manufacturer (Pharmacia). To prepare total Drosophila extract 200 flies were homogenized in 500 µl of lysis buffer (PBS+0.02% NP-40+ 0.05% Triton™ X-100+1 mM DTT+5% Glycerol+protease inhibitor cocktail) and centrifuged twice at 10,000 rpm at 4 C to clarify the extract. 100 ul of the extract (~500 ug of protein) was incubated with 25 ul of the glutathione sepharose bound GST or GST-DroGef for 1 h at 4 C with occasional stirring. The beads were collected by centrifugation at 4000 rpm for 2 min and washed three times with 500 ul of the cold lysis buffer. The bound protein was eluted in 25 ul SDS-page sample gel loading buffer, loaded into an 8% SDS-polyacrylamide gel and western blotted with 1:1000 dilution of affinity purified 273 antibodies.

Poly-A Tail Length (PAT) Assay

The polyA test (PAT) to measure the length of the polyA tail of CPEB mRNA was essentially done as described by Salles and Strickland (1999). Total RNA from the plural ganglia was digested with DNase1 and phenol: chloroform extracted. 3 ug of total RNA was reverse transcribed with 200 ng of AdT primer (5'-GCGAGCTCCGCGGC-CGCGTTTTTTTTTTTT-3') (SEQ ID NO:23) using AMV reverse transcriptase. 2 ul of the cDNA was amplified with Taq polymerase using AdT and N-actin primer 5'-GGGAAT-TCGTCTGGAGCCACCAACAC-3' (SEQ ID NO:17) in the PCR cycle: 94° C. 30 sec, 60° C. 1 min and 72° C. 1 min, 5 sec/cycle for 30 cycles. To check the amount of sensorin, Bmp1 and N-actin, the following primer pairs were used; sensorin-5'-AACAGAAACAGTC-TTTCCCCC-3' (SEQ ID NO:24) and 5'-TCTTGACTCACCAACTGCC-3' (SEQ ID NO:25), Bmp1-5'-ATCTATCGCCTATT-ATTATCACCA-3' (SEQ ID NO:26) and 5'-ATCCCATGCATTTGTTTGTT-3' (SEQ ID NO:27), N-actin 5'-CCCATCCAT-TGTCCACA-3' (SEQ ID NO:28) and 5'-TTTGAGCATTCTGGCTTC-3' (SEQ ID NO:29).

Immunocytochemistry

Following stimulation with serotonin, the cells were washed with filtered seawater and then fixed with freshly prepared 4% paraformaldehyde (PFA) in phosphate-buffered saline (PBS) plus 30% sucrose at 37° C. for 20 min. After fixation, cells were washed three times with PBS and incubated with 0.5% saponin (for isolated neurites) or 0.1% Triton X-100 (for one pulse of serotonin in the neurites) in PBS for 10 min at room temperature (RT). Subsequently cells were washed with PBS three times and excess PFA was quenched by incubating the cells in 50 mM $NH_4Cl$ in PBS for 15 min at RT. The fixed cells were blocked with a mixture of heat-inactivated 10% horse serum and 1% goat serum in PBS for 2 hr at RT, then in 1:30 dilution of affinity purified CPEB77 (for isolated neurites) or 1:100 dilution of 463 (for one pulse of serotonin in the synapse) overnight at 4° C. Next day cells were washed three times (20 min each wash) with PBS at RT before incubating with goat anti-rabbit secondary antibody conjugated with Alexa Fluor 488 (1:1000) (Molecular Probes) for 2 hr at room temperature. After three 15 min rinses with PBS cells were mounted on Fluoromount and pictures were taken at Zeiss Axiovert S-100 at 40× magnification using the program Metamorph.

Oligo Injection and TAT-Oligo Application

The antisense oilgo 5'-AAACAGAGCAGGTC-CCG-GCAGAAATAGT-3' (SEQ ID NO:30) was pressure injected into the cell. The oligo-peptide conjugate was purchased from Alta Biosciences (Birmingham, UK) and consisted of the TAT sequence (with a four glycine linker at amino terminal connecting it to a FITC) linked, via a disulfide bond, to the oligo (disulfide to the 5' end of oligo). The oligo was dissolved in water and diluted to a concentration of 100 uM in a buffer containing (as a 10× solution): 23.5 g NaCl, 0.744 g KCl, 7.14 g Dextrose, 0.192 g $NaHCO_3$ per 100 ml of solution, pH 7.6. About 0.5-1 ul of solution was perfused onto the branches for about 30 min 4 hrs prior to bath applications of 5 pulses of serotonin (all cells had prior been tested for basal EPSPs).

Cell Culture and Electrophysiology

Cell cultures and electrophysiology were done essentially as described by Montarolo et al. (1986) and bifurcated cultures as described by Martin et al. (1997). Cultures were maintained at 17° C. for 5 days prior to treatment with serotonin and electrophysiological recordings.

Results

A Neuronal CPEB in *Aplysia* and *Drosophila*

An 82 kilodalton (kd) polypeptide from *Aplysia* central nervous system RNA is homologues to *Xenopus* and CPEB. (Liu and Schwartz 2003). Unlike the *Xenopus* and mouse CPEB, *Aplysia* CPEB (ApCPEB) lacks a consensus Eg2 phosphorylation site (Mendez et al. 2000). Eg2 is a member of the Aurora family of serine/threonine protein kinases. During maturation of the *Xenopus oocyte*, Eg2 phosphorylates CPEB, which phosphorylation increases the affinity of CPEB for the cleavage polyadenylation specificity factor, CPSF160 (Mendez et al. 2000).

Figure 1B:
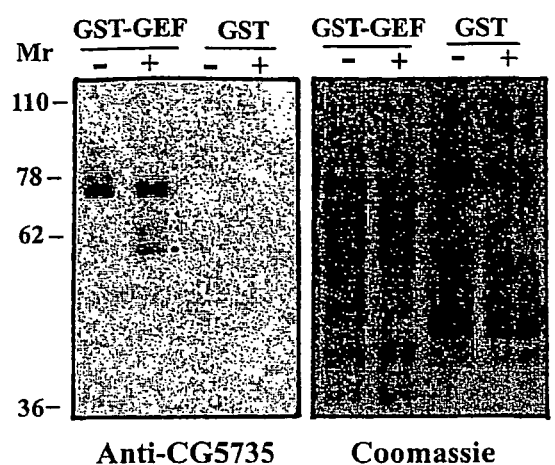
FIG. 1B: Immunoblot of *Aplysia* pleural ganglia extract and whole *Drosophila* or isolated head extracts (20 ug ea). The *Drosophila* extract showed one major band around 62 kd (*) and a minor band around 70 kd (◄). The 70 kd band could be a splice variant or some other modification of the lower band.

The human, mouse and *Drosophila* genomic databases were searched for proteins with homology to ApCPEB. In addition to the developmental isoform of CPEB (Orb) previously identified in *Drosophila*, In addition to Orb, a putative open reading frame (CG5735RA) which has an amino acid sequence and domain organization similar to *Aplysia* neuronal CPEB was identified. Unlike Orb, which is expressed throughout development, CG5735RA was not detectable in the embryonic stage. Instead, the CG5735RA mRNA was detected in the larval stages and its highest expression was detected in adult tissues, including adult brain. CG5735RA encodes a 60 kd protein (FIG. 1A) which is also expressed in the adult *Drosophila* brain (FIG. 1B). In situ hybridization further demonstrated that the CG5735RA mRNA is expressed in the mushroom bodies and the optical lobes.

Figure 1C:
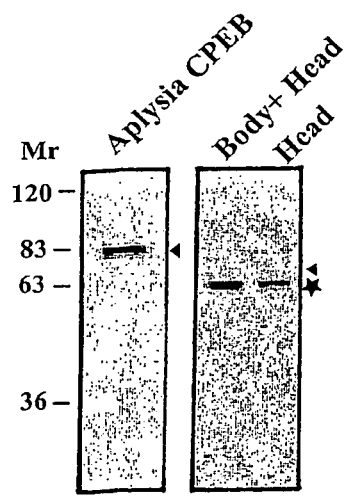
FIG. 1C: *Drosophila* rho family guanine nucleotide exchange factor DroGef interacts with *Drosophila* CG5735 protein. The recombinant GST (GST) or GST-DroGef (GST-GEF) incubated with either ~500 ug of total *Drosophila* protein extract (+) or with binding buffer alone (−), washed three times and the bound protein blotted with anti-*Drosophila* CG5735. Left panel, Western blot with affinity purified anti CG5735 antibodies; right panel, coomassie blue staining of the same membrane. Two of the immunoreactive bands in the GST-GEF lane marked with arrowheads are the 62 KD and 70 kd bands of *Drosophila* CG5735. The immunoreactive polypeptide marked with a filled circle is most likely a degradation product of the two larger polypeptides or an isoform, which became enriched in the binding reaction.

Since the *Aplysia* and the *Drosophila* proteins were isolated based on sequence homology to CPEB, we next tested whether the biochemical properties of a CPEB were conserved among these proteins. In *Xenopus* oocytes CPEB interacts with the cleavage polyadenylation specificity factor CPSF160 (Mendez et al., 2000b) and the rho family guanine nucleotide exchange factor Xgef (Reverte et al., 2003). Xgef interacts with the N-terminal half of the CPEB protein, the region where the putative neuronal. CPEB differs from the developmental isoforms. Although there is no known *Aplysia* homolog of Xgef, a *Drosophila* homologue (CG8606) has been reported (Reverte et al., 2003). The *Drosophila* XGef, DroGef, was isolated and expressed as a GST-tagged fusion protein in *E. coli*. When total *Drosophila* protein extract was incubated with purified recombinant GST-tagged DroGef, the 62 kd *Drosophila* CG5735 protein was captured (FIG. 1c). Incubation of the same cell extract with GST alone did not bring down the 62 kd protein. Thus, the *Drosophila* CPEB was able to interact with DroGef.

ApCPEB is Induced by Serotonin

To determine whether ApCPEB-dependent polyadenylation is important for long-term facilitation, we evaluated whether there is an experience dependent change in ApCPEB activity. Other isoforms of CPEB are known to be activated by phosphorylation, however, no phosphorylation of *Aplysia* CPEB was detected.

Figure 1D:
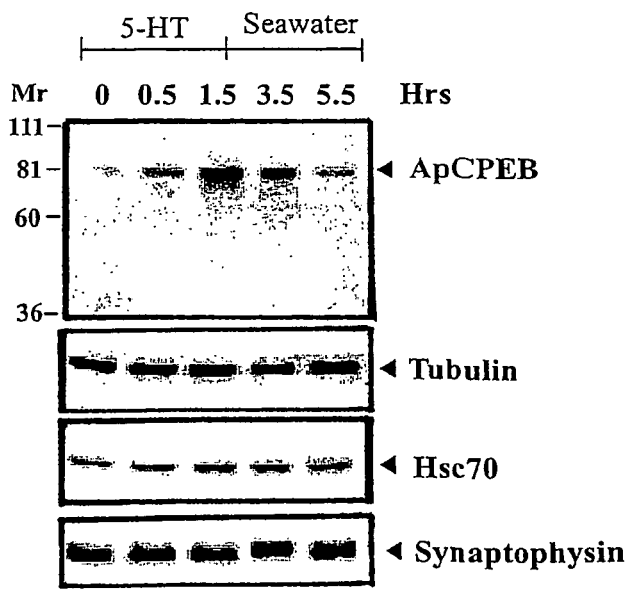
FIG. 1D: ApCPEB protein is induced by serotonin (5-HT). Western analysis of *Aplysia* pleural ganglia extracts prepared from animals exposed to 5-HT in vivo for 1.5 hr and then moved to seawater. Total cell extracts were prepared at indicated times and 10 ug of protein was immunoblotted with affinity purified anti-ApCPEB 533 antibodies (top panel). The same extracts were also blotted with synaptophysin, anti-tubulin and anti-Hsp70 antibodies as controls (bottom panel).

Alternatively, ApCPEB activity could be regulated by the amount or distribution of the protein in response to neural activity. To test this, the whole animal was exposed to serotonin for one hour followed by removal back to normal seawater, a protocol that mimics sensitization. At designated time points, cell extracts were prepared from pleural ganglia and ApCPEB was detected by Western analysis with anti-ApCPEB antibodies. As shown in FIG. 1D, thirty minutes after initiation of the serotonin treatment, the total content of ApCPEB increased 4 to 5 fold. This increased level of ApCPEB persisted for about 3 hours and returned to basal levels after five hours.

Induction of ApCPEB is Independent of Transcription But Depends on Protein Synthesis The induction of ApCPEB protein within one hour after the initiation of serotonin treatment raised the question of whether it is a transcriptionally induced early gene or whether it is regulated post-transcriptionally. To address this question, the sensory cells of the pleural ganglia were pretreated with inhibitors of transcription or translation before stimulation with serotonin. As with the whole animal, treatment of the isolated pleural ganglia with 10 uM 5-HT increased the total CPEB content by 3-4 fold. As shown in FIG. 2A, pretreatment with the transcription inhibitors α-amanitin (50 ug/ml) or actinomycin D (10 ug/ml) did not block the induction of ApCPEB. In contrast, these transcription inhibitors completely blocked the induction of *Aplysia* ubiquitin hydrolase (ApUbh), a 5-HT responsive transcriptionally induced gene (data not shown) (Hegde et al. 1997). Similarly, when semi-quantitative RT-PCR was used to analyze the amount of ApCPEB mRNA present in the sensory cells of the pleural ganglia, no significant difference was found between 5-HT treated and untreated samples. In contrast, the induction of ApCPEB protein by 5-HT was reduced in the presence of the protein synthesis inhibitor emetine (100 uM) and cycloheximide (40 uM) (FIG. 2B).

Rapamycin, which inhibits translation of a specific set of mRNAs, selectively blocks the maintenance phase of long-term plasticity when locally applied to a synapse (Casadio et al. 1999). To test whether the serotonin induction of ApCPEB was partially due to an increase in translation, pleural ganglia were pretreated for 30 min with 20 nM rapamycin. As shown in FIG. 2C, rapamycin blocked the serotonin-induced increase in ApCPEB.

Poly(A) Tail of Neuronal F-Actin mRNA Increases in Response To Serotonin

Figure 3A:
FIG. 3A: (SEQ ID NO: 33; SEQ ID NO: 34) Neuronal actin mRNA is a target of ApCPEB. Schematic of the PolyA tail length (PAT) assay. PolyA RNA was reverse transcribed with dT-Adaptor™ primer and the first strand cDNA was amplified with an N-actin specific primer and Adaptor primer 3' of the polyA tail.
Figure 3B:
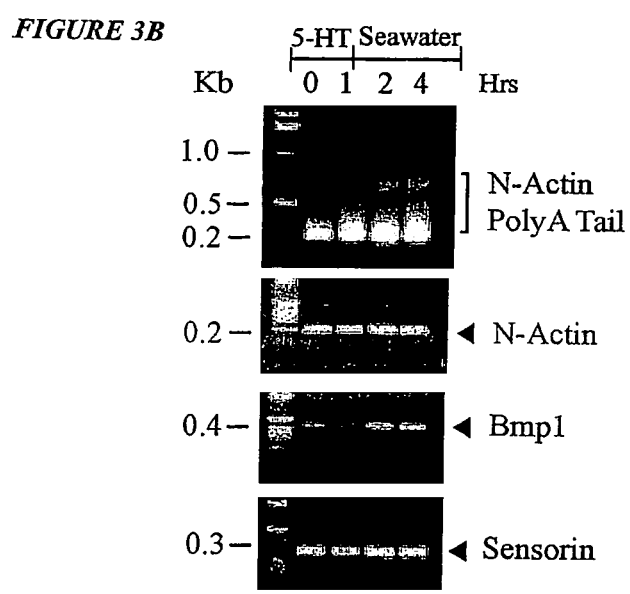
FIG. 3B: PAT assay of N-actin mRNA isolated from stimulated *Aplysia* pleural ganglia. Total RNA was isolated at the indicated times from pleural ganglia and the PAT assay products were analyzed on a 1.8% agarose gel. Elongation of the polyA tail length increases the size of the PCR product. Two N-actin specific primers were used to quantitate the total amount of N-actin mRNA in each sample. The 5-HT responsive bone morphogenetic protein mRNA (Bmp1) is used as 5-HT stimulation control. Sensorin, a sensory cell specific gene, is used as PCR control.

*Aplysia* neuronal actin mRNA was identified as having a polyadenylation signal (AAUAAA) and a putative CPE (UUUUUUAU) (Liu and Schwartz 2003). To investigate whether N-actin is a potential target of ApCPEB in the process of long-term facilitation, the effect of repeated pulses of serotonin, which induces CPEB, on its poly(A) tail length was examined. As noted above, serotonin induces either short- or long-term facilitation depending on the stimulation protocol. A PCR based PAT assay (Salles et al. 1999) was used to measure changes in the poly(A) tail of N-actin following whole-animal stimulation with serotonin and isolation of mRNA from neural ganglia. As shown in FIG. 3B, within an hour after the initiation of treatment with serotonin the poly (A) tail of N-actin increased by 200-400 nucleotides and was sustained for at least 4 hours. The polyadenylation of *Aplysia* neuronal actin mRNA has also been reported by others (Liu and Schwartz 2003).

It was evident from these experiments that only a fraction (5-10%) of the neuronal actin mRNA was polyadenylated. This could be due to compartmentalization of the mRNA, such that only a fraction of neuronal actin mRNA may be accessible to the machinery for polyadenylation. The change in poly (A) tail length was not due to a difference in the mRNA content as there were equivalent amounts of neuronal actin mRNA in the stimulated and unstimulated cells. The time course of the change in the poly (A) tail length of N-actin coincides with the time course of induction of ApCPEB. This strongly suggests that neuronal actin may be one of the genes whose synthesis is controlled by ApCPEB.

ApCPEB is Induced in the Neurites by One Pulse of Serotonin

Since the increase in the level of ApCPEB is sensitive to rapamycin and one of the targets of ApCPEB is N-actin, a molecule implicated in synaptic remodeling and growth, we asked whether ApCPEB constitutes a component of a rapamycin sensitive synaptic mark. We therefore sought to determine whether ApCPEB had the properties of a mark defined by Casadio (Casadio et al. 1999). We wanted to know whether a single pulse of serotonin could stimulate the synthesis of ApCPEB? If so, could it do so locally in the neurites?

Figure 4A:
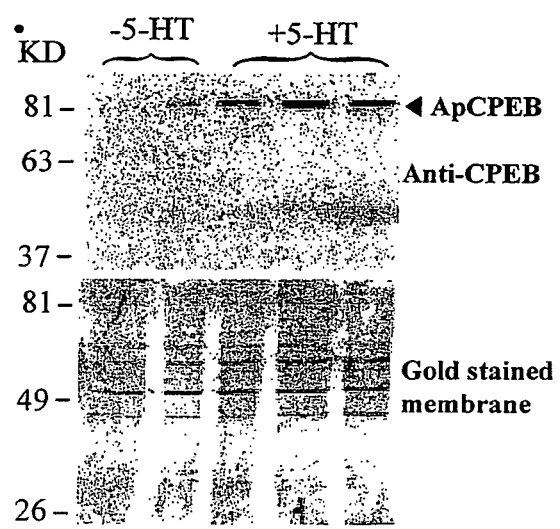
FIG. 4A: ApCPEB is induced by one pulse of 5-HT in the sensory cell neurites. Western blot of *Aplysia* pleural ganglia stimulated with 10 uM 5-HT for 10 min. Total protein visualized by gold staining is shown as a loading control.
Figure 4B:
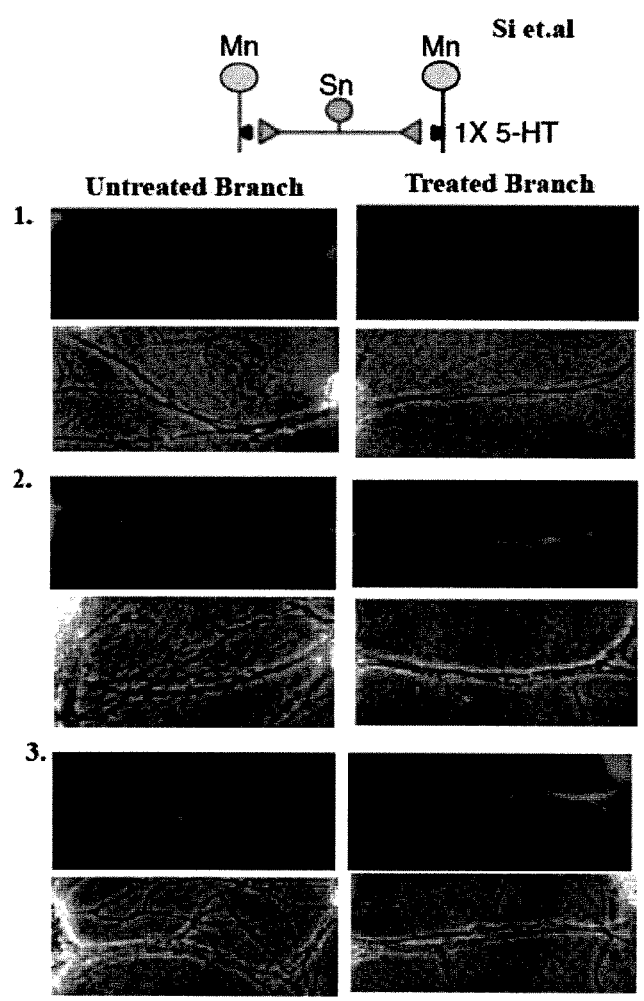
FIG. 4B: ApCPEB induction is restricted to the stimulated neurite. One branch of the sensory-motor bifurcated culture was stimulated (right branch) with one pulse of 10 uM 5-HT. An hour after the stimulation the cells were fixed and immuno-stained with either preimmune serum (b1) or Anti-CPEB serum 533 (b2 and b3—two independent examples). The phase contrast image of the sensory cell neurites is shown under the fluorescence image. Only the neurites of the sensory cells are shown.

When the sensory cell clusters of pleural ganglia were exposed to 10 uM 5-HT for 10 min, then moved to seawater for additional 50 min, a 4-5 fold increase in the total ApCPEB protein content was observed. This is as much as we have observed after continuous treatment with 5-HT for an hour (FIG. 4A). A "single pulse" of 5-HT, as used in electrophysiological studies, typically consists of five 10 second pulses of 10 uM 5-HT with a 10 second interval between pulses. Accordingly, a "single pulse" of 5-HT was tested for its ability to induce ApCPEB. 10 uM 5-HT was applied for 50 seconds to one branch of a bifurcated culture system in which a single sensory neuron makes synaptic contacts with two spatially separated L7 motor neurons. After one hour, the cells were fixed for immunostaining with anti-*Aplysia* CPEB antibodies. A selective, localized increase in ApCPEB immunoreactivity was observed in the branch stimulated with 5-HT (average fluorescence intensity in the treated branch is $53.3 \pm 8.7$ and that in the untreated branch is $37.7 \pm 5.2$, n=10) (FIG. 4B). This result also revealed that once induced *Aplysia* CPEB remains restricted mostly in the stimulated branch and does not disperse through out the cell.

Figure 4C:
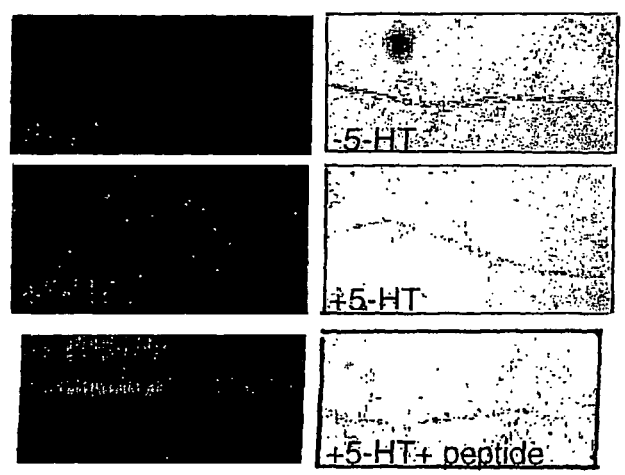
FIG. 4C: ApCPEB can be induced in isolated neurites. Cell bodies of the sensory-motor neuron were cut off and then stimulated with 10 uM 5-HT for an hour. The neurites were fixed and ApCPEB was detected by immunostaining with ApCPEB77. Top panel, untreated; middle panel, treated with 5-HT; bottom panel, 5-HT treated neurites stained with ApCPEB77 preincubated with the blocking peptide; left panels, fluorescence image; right panels, phase contrast image.

To resolve the issue of whether the induction of ApCPEB occurs locally in the neurites, sensory cells were cultured with their target motor neurons for 5 days then severed at the cell body. The isolated sensory neurites were then stimulated for 1 hr with bath application of 10 uM 5-HT and subsequently fixed for immunocytochemistry. Immunostaining with anti-ApCPEB antibodies revealed a significant increase in the ApCPEB immunoreactivity localized to the stimulated neurites (average fluorescence intensity $9.37 \pm 0.73$, n=8) when compared to non-stimulated neurites (average fluorescence intensity $2.84 \pm 0.63$, n=9) (FIG. 4C). This induction of ApCPEB immunoreactivity was blocked when the neurites were stimulated with 5-HT in the presence of 20 nM rapamycin (average fluorescence intensity $0.77 \pm 0.1$, n=9). Moreover, when we sequenced a cDNA library prepared from isolated sensory cell neurites, we found *Aplysia* CPEB mRNA. The presence of the ApCPEB mRNA in the neurites is consistent with the fact that it can be synthesized locally in the neuritis.

ApCPEB Induction is Independent of PKA Activity But Dependent on PI3 Kinase Activity The synaptic mark is not only sensitive to rapamycin, but also to inhibitors of PKA, and the initiation of serotonin mediated long-term facilitation requires activation of PKA. Accordingly, the requirement for PKA activation in the serotonin induced expression of ApCPEB was examined. As shown in FIG. 5A, pretreatment of sensory clusters with the PKA inhibitor KT5720 did not block the serotonin induced increase in ApCPEB. Activation of PKA by a cell permeable analog of cAMP, SpcAMP, did not change the level of ApCPEB (data not shown). These results indicate that the serotonin induced increase in ApCPEB protein is not PKA-dependent.

These results suggest that the initiation and maintenance of serotonin mediated long-term facilitation occurs through two different signal transduction pathways. The initial phase is mediated by PKA while the maintenance phase, which involves the synthesis of ApCPEB, is sensitive to rapamycin and is independent of PKA activity.

*Aplysia* serotonin mediated activation of rapamycin sensitive pathways depends on the activity of protein kinase C (PKC) (Khan et al. 2001). However, treatment of sensory cells with the PKC inhibitor, chelerythrine (10 uM), did not affect the serotonin dependent increase of the ApCPEB protein (FIG. 5B). In non-neuronal cells, the rapamycin sensitive pathway may also be regulated by PI3 kinase (Gingras et al. 2001). As shown in FIG. 5C-D, the PI3 kinase inhibitor, LY294002 effectively blocked the serotonin induced expression of ApCPEB. Thus, the serotonin dependent increase in ApCPEB requires PI3 kinase activity.

PI3 kinase activity is required for LTP in the hippocampal CA1 region (Raymond et al. 2000; Sanna et al. 2002), in the amygdala and in the dentate gyrus (Kelly et al. 2000; Yang et al. 2001). Interestingly, our results suggest that PI3 kinase is not needed for the induction of LTP but rather for its maintenance.

ApCPEB is Required at the Synapses for the Late Phase of Long-Term Facilitation

Figure 6A:
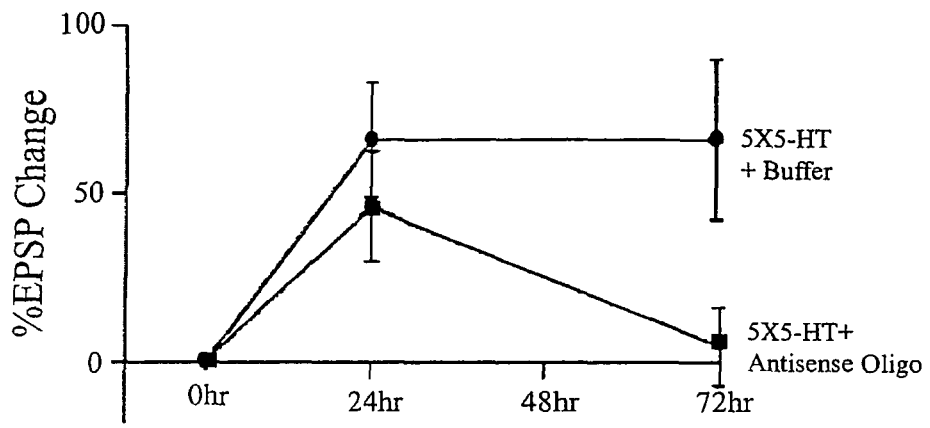
FIG. 6A: ApCPEB is needed for stabilization, not for the induction of LTF. A 16 nucleotide antisense oligo designed from ApCPEB mRNA was injected into the cell body and cells were stimulated by bath application of 5 pulses of 10 uM 5-HT. To measure long-term facilitation, EPSPs were recorded in L7 motor neurons 24 hr (LTF) or 72 hr (late-phase LTF) after 5-HT treatment. Uninjected cells are facilitated at both 24 and 72 h. Cells injected with antisense oligo are facilitated at 24 h, but not at 72 h.

The requirement for ApCPEB activity in serotonin induced synaptic facilitation was assessed using antisense oligonucleotides that selectively bind to and degrade ApCPEB mRNA, thereby inhibiting the synthesis of the protein. Either antisense oligo or its vehicle was microinjected into a sensory cell prior to stimulation with five pulses of serotonin. As shown in FIG. 6A, cells receiving vehicle exhibited an increase in the mean amplitude of the EPSP in the sensory-motor neuron connection at 24 hrs (% EPSP+$66.4 \pm 14$, n=17) which persisted for 72 hrs (% EPSP+$66.5 \pm 23.4$, n=12). Cells receiving ApCPEB antisense oligonucleotides also exhibited an increase in the mean EPSP amplitude at 24 hrs (% EPSP+$30.6 \pm 17.3$, n=23), although reduced compared to the cells receiving vehicle. However, this facilitation was not persistent and instead returned to baseline at 72 hrs (% EPSP+$4.7 \pm 11.5$, n=19). This suggested that the ApCPEB activity is primarily needed for long-term maintenance of facilitation, rather than for the initiation of synaptic events that lead to facilitation during the first 24 hours.

Since the injection of antisense oligonucleotides into the cell body inhibits the function of ApCPEB throughout the cell, the above experiments did not address whether CPEB activity is important at the activated synapses. To selectively block ApCPEB only in activated synapses, a method was needed to deliver the ApCPEB antisense oligonucleotides to the synapses directly. This was accomplished by covalently coupling the oligonucleotides to an 11 amino acid peptide derived from the HIV-TAT protein, TAT-AS (Schwartz and Dowdy 2000). The resulting fusion protein demonstrated enhanced cell permeability. Initially, the ability of the TAT-antisense oligo to inhibit CPEB synthesis was examined. Sensory cells were treated with bath application of TAT-antisense oligo or TAT-scrambled oligo and ApCPEB was measured by immunohistochemistry. In the cells treated with TAT-antisense oligo, a selective decrease in the CPEB immunoreactivity was observed.

Figure 6B:
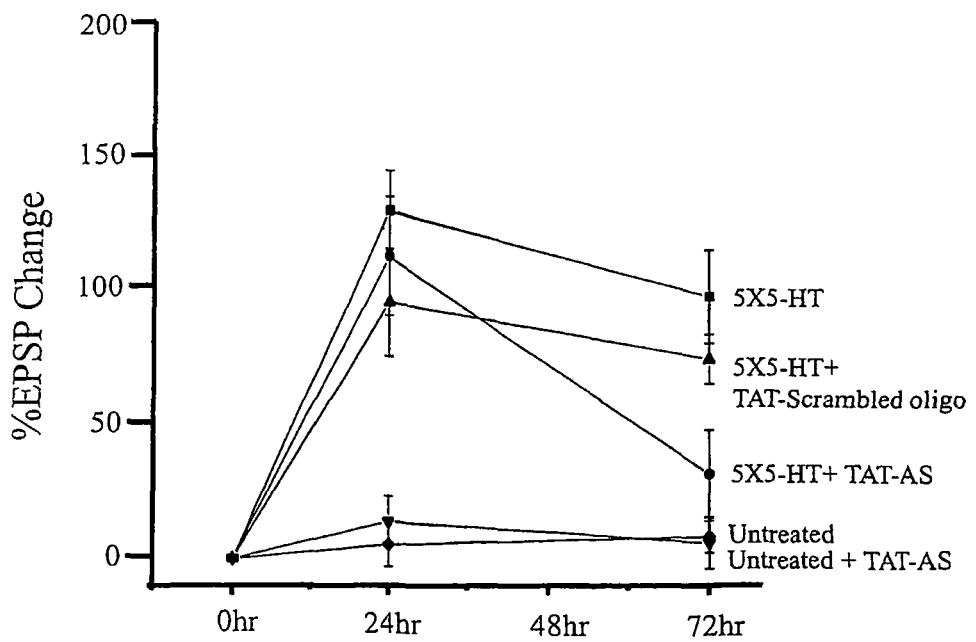
FIG. 6B: Local inhibition of CPEB can block stabilization of LTF. TAT-ApCPEB peptide-oligo was perfused at the synapse for 30 min, and cells were stimulated by bath application of 5-HT. EPSPs were recorded in L7 motor neuron at 24 hr and 72 hr.

As shown in FIG. 6B, perfusion of the TAT-AS to the synapse did not interfere with the basal synaptic transmission of the sensory-motor neuron synapses (% EPSP+$13.5 \pm 9.4$; n=6) when compared to untreated control synapses (% EPSP+$11.4 \pm 23.6$; n=6). ApCPEB was inhibited locally by perfusing TAT-AS to one branch of a bifurcated sensory neuron for 30 min prior to stimulation of both branches by bath application of five pulses of serotonin. This protocol produced a long-term synaptic facilitation in the control branch that persisted up to 72 hr (% EPSP at 24 hr+128±14.6, at 72 hr+96.8±17.3; n=17, FIG. 6B). In the branch that received TAT-AS, a long-term facilitation was initiated that was indistinguishable from that of control (% EPSP at 24 hr+119±22.0; n=17). However, this facilitation largely disappeared by 72 hours (% EPSP+30.9±16.1; n=17). Perfusion of the control scrambled oligonucleotide-TAT fusion peptide did not interfere with serotonin dependent facilitation at 24 h (% EPSP at 24 h+94.7±20.0; n=10) or its maintenance until 72 h (% EPSP+73.6±9.2; n=10). Thus, the activity of synaptic ApCPEB is necessary for the maintenance of long term facilitation, but not for its induction. Moreover, since the antisense oligo causes only local degradation of the ApCPEB mRNA, these results provide independent evidence that ApCPEB is locally translated in the synapses. Also, diffusion of the antisense-oligo to the cell body and resulting inhibition of CPEB synthesis should have prevented facilitation in both branches. Taken together these experiments indicate that the local activity of CPEB in the presynaptic sensory cell is required for the maintenance of long-term facilitation.

However, the locally applied TAT-antisense oligo can also inhibit the CPEB function (if there is any) in the post-synaptic motor neuron. Thus it is possible that the CPEB activity in the post-synaptic neuron is also required for the maintenance of long-term facilitation.

Discussion

The results presented here identify the *Aplysia* homologue of the cytoplasmic polyadenylation binding protein as a component of the synaptic mark that is required for stabilization of synapse specific facilitation. These results also distinguish ApCPEB as a neural specific isoform of CPEB that is regulated differently than the CPEB isoform present in maturing oocytes. In maturing oocytes, CPEB is activated via phosphorylation by the Eg2 kinase. However, ApCPEB lacks the consensus phosphorylation site of Eg2. Instead, the results presented here suggest that ApCPEB is regulated post-transcriptionally via a PI3 kinase-dependent signal.

CPEB Activity in Neurons Might be Regulated by Distinct Mechanisms

In maturing oocytes, phosphorylation of CPEB by Eg2 at a canonical LDS/TR site (Mendez et al. 2000) induces the recruitment of the multisubunit cleavage and specificity factor CPSF to the polyadenylation signal AAUAAA (Mendez et al. 2000a). The recruitment of CPSF in turn most likely engages the PolyA polymerase (PAP) leading to the elongation of the PolyA tail. The CPEB dependent polyadenylation machinery, including Eg2, is also present in the synapses of cultured hippocampal neurons and stimulation of these neurons with glutamate leads to polyA elongation of the CamKII mRNA (Huang et al. 2002).

In contrast, the neuronal isoform of *Aplysia* CPEB does not have a LDSR site or its variant LDSH. While the absence of a canonical phosphorylation site does not formally rule out the possibility that there might be other phosphorylation sites, no phosphorylation of *Aplysia* CPEB has been observed thus far (our unpublished observation). Indeed the activity dependent translation of the synaptic *Aplysia* CPEB mRNA suggests other ways of controlling the activity of ApCPEB. Recently, several CPEB-like molecules have been identified from the genomic sequences of human, mouse and *Drosophila* (Mendez and Richter 2001). Some of these resemble the *Aplysia* CPEB in that they lack the Eg2 phosphorylation sites. It will be interesting to know whether CPEB molecules that lack the Eg2 phosphorylation sites also represent neuron specific isoforms of CPEB. If that were so, it would imply that the regulation of CPEB activity at the synapse might have a distinct mechanism from that of activation of CPEB during early developmental stages. However, it is also possible that the both phosphorylation dependent and independent pathways can be operative in neuronal cells.

ApCPEB Stabilizes Long-Term Synaptic Facilitation

The neuronal isoform of *Aplysia* CPEB is translated locally following even a single pulse of serotonin and the newly synthesized CPEB is critical for stabilization of the LTF. How might ApCPEB stabilize this late phase? Long-term facilitation involves both structural reorganization of preexisting facilitated synapses as well as growth and establishment of new synaptic connections (Bailey et al. 1991). Reorganization and growth of new synapses has two broad requirements: (1) structural (changes in shape, size and morphology) and (2) regulatory (where and when to grow). The genes involved in both of these aspects of synaptic growth might be potential targets of ApCPEB. The structural aspects of the synapse are dynamically controlled by reorganization of the cytoskeleton, which can be achieved either by redistribution of preexisting cytoskeleton components or by their local synthesis. The observation that *Aplysia* N-actin and $T\alpha 1$ tubulin mRNAs are present in and can be polyadenylated in response to serotonin suggests that at least some of the structural components for synaptic growth can be controlled through CPEB mediated local synthesis (Kim and Lisman 1999). In addition, CPEB has been found to be involved in the regulation of local synthesis of EphA2 (Brittis et al. 2002), a member of a family of receptor tyrosine kinases. Local synthesis of EphA2 is needed for axonal pathfinding. Mammalian Eph receptors are involved in a variety of processes, such as establishment of neuronal identity, neuronal pathfinding, and formation of excitatory synapses. Another Eph receptor family member, EphB2, is induced in pyramidal neurons by stimuli known to induce changes in synaptic structure (Contractor et al. 2002; Henderson et al. 2001). Thus, CPEB might contribute to the stabilization of learning related synaptic growth by controlling the synthesis of both structural molecules such as tubulin and N-actin and regulatory molecules such as members of the Ephrin family.

ApCPEB is a Component of the Rapamycin Sensitive, Protein Synthesis-Dependent Mark Casadio et al. suggested that the rapamycin sensitive component of synaptic mark should have the following properties: 1) it should be made or activated by a signal for short-term facilitation at the synapse; 2) it should be dependent on the activity of a rapamycin sensitive signaling pathway; 3) it should be stable for 3-4 hrs from the time of initiation; and 4) inhibition of the activity of the mark should influence specifically the late phase of the LTF not its initiation.

We have found that *Aplysia* CPEB qualifies as a component of the mark on all of these criteria. Moreover, the fact that inhibitors of PKA did not block induction of CPEB suggests that the PKA-dependent and local protein synthesis-dependent components of the mark occur in parallel rather than sequentially. A parallel arrangement of these marking components could further serve as a cellular gatekeeping mechanism that ensures that not every short-term change which activates PKA will be stored for the long-term.

The PI3 kinase activity is required for LTP in the hippocampal CA1 region (Raymond et al. 2002; Sanna et al. 2002), in the amygdala and in the dentate gyrus (Kelly et al. 2000; Yang et al, 2001). Interestingly, these studies suggest that PI3 kinase is not needed for the induction of LTP but seems to be specifically important for its maintenance. This is consistent with our observation that PI3 kinase is required for the induction of CPEB, which regulates the maintenance phase of long-term facilitation. This raises the intriguing possibility that in mammalian brain as in *Aplysia* one of the consequences of PI3 kinase activation might be the activation of CPEB dependent local protein synthesis.

These results suggest a model of synaptic marking in which a single pulse of serotonin activates the PI3 kinase pathway, which in turn leads to the activation of a rapamycin signaling pathway, resulting in the synthesis of ApCPEB. Newly made CPEB then recruits the polyadenylation machinery important for activating two types of molecules: (1) structural molecules important for synaptic growth, such as N-actin and (2) potentially regulatory molecules that determine where and how much to grow.

Prion-Like Properties of *Aplysia* CPEB

The following demonstrates that the ApCPEB N-terminal domain can confer upon other proteins and upon CPEB itself the properties of a prion-like protein. The findings in yeast raise the possibility that a prion-like state of CPEB might selectively sustain an altered state of translation locally, at some synapses and not at others, and thereby contribute to the long-term maintenance of a self-sustaining synapse-specific change.

The N-Terminal Region of ApCPEB has the Features of a Prion Determinant

Figure 7A:
FIG. 7A: (SEQ ID NO: 31) Sequence of the glutamine (Q)/asparagine (N) rich N-terminal 160 amino acids of ApCPEB. The imperfect repeat sequence QQQL (SEQ ID NO:32) is underlined.

The amino-terminal end of *Aplysia* CPEB has an unusually high content of the amino acids glutamine and asparagine (Q+N). For example, the N-terminal 160 amino acids of 44 randomly selected *Aplysia* proteins have an average glutamine+asparagine (Q+N) content of 10%, typical of proteins in other species. In contrast, the N-terminal 160 amino acids of ApCPEB, have a (Q+N) content of 48% (FIG. 7A). The *Aplysia* CPEB N-terminal domain also resembles yeast prion domains in lacking predictable secondary structure. A search of the protein-sequence database revealed putative homologues of this specific neuronal isoform of CPEB in *Drosophila* and humans, with N-terminal extensions of similar character. The *Drosophila* protein, CG5735 alt1, has a (Q+N) content of 35% for its N-terminal 82 amino acids. The human protein, KIAA0940, has an 18% (Q+N) content for its N-terminal 205 amino acids. The N-terminal domains of both the *Drosophila* and the human protein also have no predictable secondary structure. The conservation of a CPEB isoform with such an N-terminal extension suggests it has, an evolutionarily conserved function. Since many rigorous tests for prions are available in yeast cells, we employed yeast as a model system for the further characterization of the prion-like properties of ApCPEB.

One test of a prion determinant is the ability to confer upon another protein to which it is fused, a capacity to exist in distinct physical and functional states that are inter-convertible and heritable. As previously described for NM, the prion-determining region of Sup35 (Li and Lindquist 2000), we fused the N-terminal 160 amino acids of ApCPEB (CPEBQ) to the green fluorescence protein (GFP). GFP is normally soluble in yeast. The fusion conferred a capacity to exist in distinct states. Large aggregates, small aggregates or soluble protein and mother cells almost always gave rise to daughter cells with the same protein distribution.

Figure 7B:
FIG. 7B: Schematic of ApCPEB N-terminal 160 amino acid and glucocorticoid receptor (CPEBQ-GR526) fusion construct. The fusion construct was expressed under a constitutive GPD promoter. CPEBQ-GR526 gives rise to metastable blue and white cells. W303a cells were transformed with plasmids bearing CPEBQ-GR526 [TRP1] and GRE-β-gal [LEU2]. Leu+ Trp+ double transformants were selected and replica plated onto -Leu-Trp+2% X-Gal-containing plates. Representative CPEBQ-GR526 blue and white cells are shown. The inset shows spontaneous conversion of the white cells to blue and blue to white.

Next, we fused the N-terminal domain to a constitutively active variant of the rat glucocorticoid receptor ($GR^{526}$) (FIG. 7B). The activity of the fusion protein is easily assayed by its introduction into cells containing a β-galactosidase gene under the control of a glucocorticoid response element (GRE). If the glucocorticoid receptor is active, it will bind to and activate transcription from the GRE, producing β-galactosidase. If the cells are cultured on plates containing the chromogenic substrate, X-gal, the activity of β-galactosidase is easily monitored from the appearance of a blue color. Thus, this system provides a convenient blue-white colony color assay for glucocorticoid receptor activity (Li and Lindquist 2000).

As shown in FIG. 7B, most cells expressing the fusion protein, CPEBQ-$GR^{526}$, were blue and remained blue from generation to generation, indicating that the transcriptional activity of the glucocorticoid receptor fused to CPEBQ remained intact. As is the case for most yeast prions and for the NM-GR prion, the CPEBQ-GR activity had a metastable character. Blue colonies occasionally (~0.0001%) gave rise to white colonies. These white colonies continued to give rise to white colonies for generations upon restreaking, but occasionally gave rise to blue colonies again. In contrast, the glucocorticoid receptor alone very rarely produced white colonies, and when it did, these never produced blue colonies again.

Figure 7C:
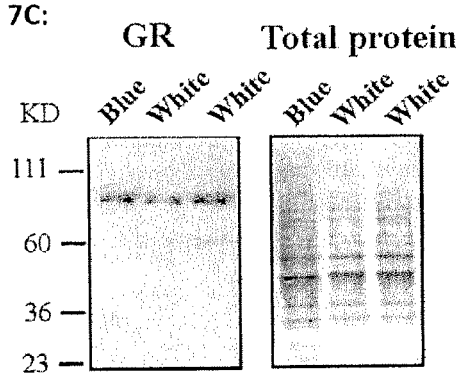
FIG. 7C: A similar amount of GR protein is present in both cell types. Total cell lysates were prepared from CPEBQ-GR526 blue and white cells. 50 ug of total protein was immunoblotted with anti-rat GR monoclonal antibody (left panel). The membrane blotted with anti GR antibody was also stained with coomassie blue to visualize the total protein content of each sample (right panel). Molecular weight standards are indicated at left.

Analysis of plasmids extracted from blue and white CPEBQ-$GR^{526}$ colonies, and of the cells themselves after loss of the plasmids, demonstrated that the changes in glucocorticoid receptor activity in blue and white cells were not due to mutations in either the plasmids or the cellular genomes. As shown in FIG. 7C, the amount of glucocorticoid receptor protein produced by the white and blue colonies was similar. These results indicated that CPEBQ fused to the glucocorticoid receptor conferred on the receptor the ability to exist in two functionally distinct states that were heritable and inter-convertible at low frequency.

Figure 8A:
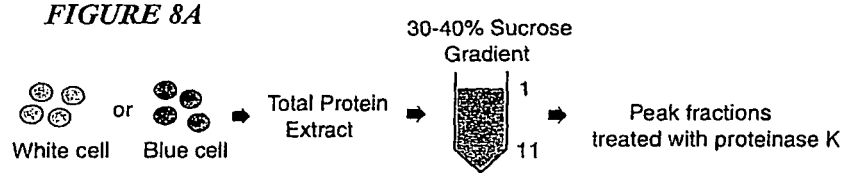
FIG. 8A: The N-terminal domain has two distinct physical states. A schematic representation of the experimental procedure is shown.
Figure 8B:
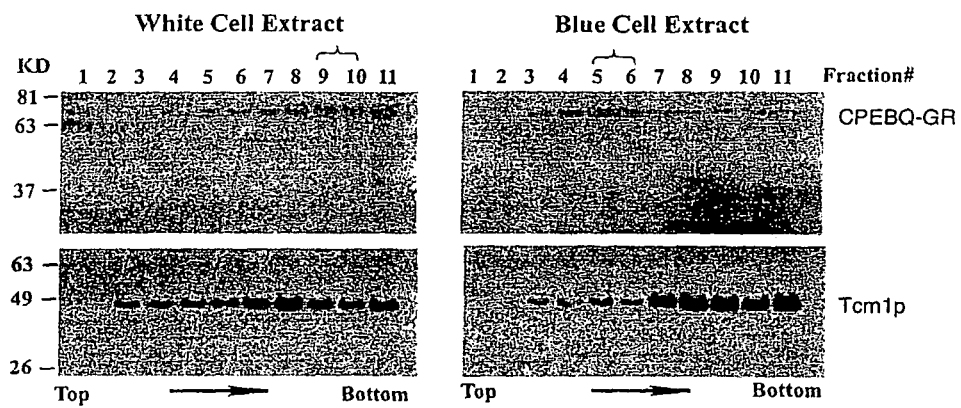
FIG. 8B: CPEBQ-GR526 protein has a different sedimentation velocity in blue versus white cells. Total cell extracts (~1 mg of protein) from blue or white cells were analyzed in a 30-40% sucrose gradient (W/V) by ultra centrifugation at 140,000×g for 1 hr 45 min at 4° C. Following centrifugation, the gradient was fractionated and immunoblotted for GR (Top panel) or 60S ribosomal protein Tcm1P (Bottom Panel).

Distinct Functional States of CPEBQ-GR are Associated with Distinct Physical States And Are Transmissible To test directly if the distinct heritable functional states of CPEBQ-$GR^{526}$ were associated with distinct physical states of the protein, we examined its sedimentation behavior and resistance to protease digestion. When extracts were analyzed on step gradients of 30-40% sucrose at 140,000×g the CPEBQ-$GR^{526}$ proteins of blue and white colonies behaved very differently. The former were concentrated in the middle of the gradient, the latter towards the bottom (FIG. 8B). In the same experiment, the distribution of other yeast proteins, such as the 60S ribosomal protein, Tcm1p (FIG. 8B, bottom panel), a Golgi associated protein Bet3p (data not shown), and total Coomassie stainable material, was similar in blue and white cells.

Figure 8C:
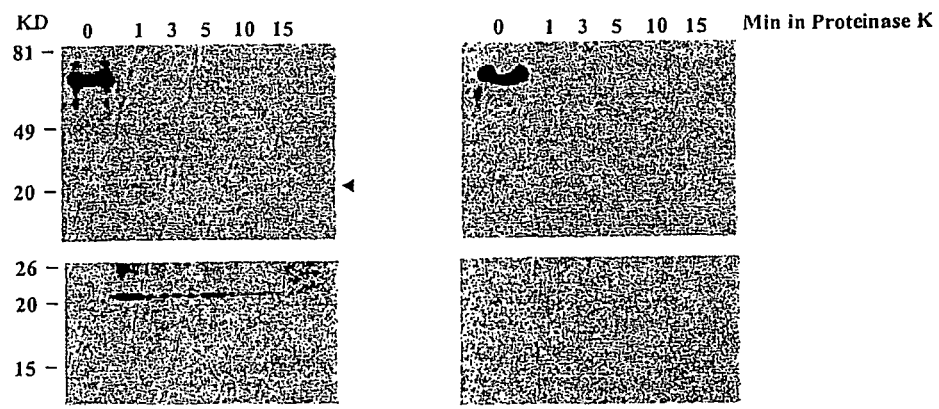
FIG. 8C: Protease resistance of CPEBQ-GR526 in white cells. The peak gradient fractions (tube#5&6 from the blue cell gradient and tube#9&10 from the white cell gradient) were pooled, treated with 100 ng of proteinase K for the indicated times and analyzed by western blotting for GR with rabbit anti-GR polyclonal antibodies. Top panel, 10% SDS-PAGE optimized for the separation and transfer of the full length CPEBQ-GR. Bottom Panel, 12.5% SDS-PAGE optimized for low molecular weight protease resistance fragment. The proteinase K resistance fragment in the white cell extracts is also detectable in the top panel (◄).

Next, peak fractions containing CPEBQ-$GR^{526}$ were equalized for total protein concentration and treated with 0.1 ug of proteinase K (FIG. 8C). With proteins derived from blue colonies, all immunoreactive CPEBQ-$GR^{526}$ polypeptide disappeared within 1 min. In contrast, with proteins derived from white cells an immunoreactive fragment of ~22 KD appeared early in digestion and persisted for at least 10 min (FIG. 8C top and bottom panels).

Figure 7D:
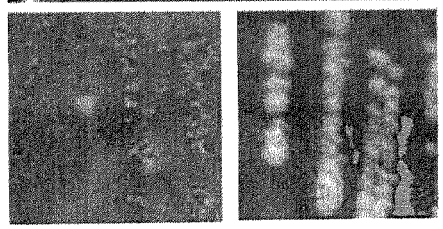
FIG. 7D: ApCPEB N-terminal domain has a dominant conformational state. The CPEBQ-GR526 was cloned into two different plasmids, one with HIS3 marker and the other with TRP1 marker. W303α cells were transformed with CPEBQ-GR526 HIS3 plasmid and W303a cells were transformed with CPEBQ-GR526TRP1 plasmid. White cells were selected from W303a Trp+ Cells (left panel) and blue cells were selected from W303α His+ cells (middle panel). W303a and W303α cells were mated and the His+ Trp+ diploids were selected (right panel). The a/α diploid were than replica plated in 2% X-Gal containing plates. This mating produced white cells.

The defining feature of prion-like propagation in yeast is the ability of protein in the prion state to induce other proteins carrying the same prion domain to enter the prion state, thereby self-perpetuating the prion form. For NM-GR fusions, when the protein enters the prion state, it forms large complexes (Li and Lindquist, unpublished), GR activity is lost, and this loss of activity is dominant in crosses to cells with active NMGR that is not in a prion state (Li and Lindquist, 2000). The physically distinct, inactive state of CPEBQ-$GR^{526}$ behaved like a prion: its loss-of-function phenotype had the same unusual dominant character. When haploid cells producing active CPEBQ-$GR^{526}$ (His+ blue cells) were mated to cells producing inactive CPEBQ-$GR^{526}$ (Trp+ white cells) all Trp+His+ diploids were white and remained white upon re-plating (FIG. 7D).

These data support the conclusion that the N-terminal domain of *Aplysia* CPEB confers upon the glucocorticoid receptor fusion protein the ability to exist in distinct functional and physical states that are heritable, inter-convertible, and transmissible in the manner of a prion-like protein.

Full-Length ApCPEB Protein can Exist in Two Functionally Distinct Heritable States To determine if the N-terminus of ApCPEB could behave like a prion in the context of native CPEB, an assay was developed to score the activity of the full-length protein in yeast, based on the following rationale. The translational activation by CPEB can be broken down into two broad activities, recognition or binding of CPEB to CPE and the recruitment of the polyadenylation machinery via its interaction with CPSF160. There is no functional homologue of CPEB in yeast. However, the components of the core polyadenylation machinery (including CPSF160) in yeast are functionally and structurally homologous to that of mammalian cells (Shatkin and Manley 2000). We reasoned that because of the structural and functional similarity between the yeast and mammalian PolyA, CPEB expressed ectopically might recruit the polyadenylation machinery, which in turn could translationally activate mRNAs containing CPE.

A 78 nucleotide fragment from the 3'UTR of *Xenopus* cyclin B1 mRNA contains a canonical CPE binding element, UUUUUAAU, and a polyadenylation element, AAUAAA, that is sufficient for CPEB-dependent polyadenylation (de Moor and Richter, 1999).

Figure 9A:
FIG. 9A: An assay for ApCPEB activity in yeast. Schematic diagram of β-galactosidase Xenopus cyclin B13' UTR fusion construct (β-gal-CPE) The 3'UTR of the reporter construct is comprised of 393 nucleotides of the SV40 3'UTR and 78 nucleotides of the cyclin B13'UTR containing a CPE element, UUUUUAAU, and a hexanucleotide polyadenylation signal, AAUAAA.
Figure 9B:
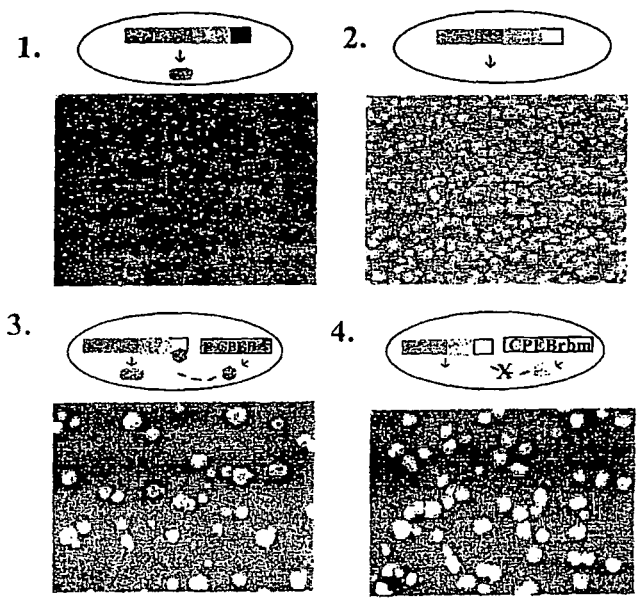
FIG. 9B: W303a cells transformed with either β-gal-SV40-SynCAM3UTR (1), with β-gal-SV40-CPE (2), with β-gal-SV40-CPE and p9214-ApCPEB (3) or with β-gal-CPE and p9214-ApCPEBrbm (4). Transformants were plated on a 2% X-Gal plate and photographed after 2 days.
Figure 9C:
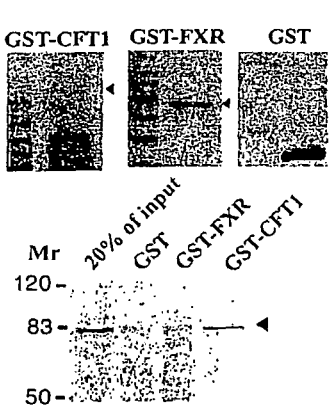
FIG. 9C: Aplysia CPEB interacts with the yeast Cstf1. GST pull-down experiment. Top Panels: Coomassie blue staining of recombinant purified GST-Cft1-$H_6$ (see methods for detail), GST-FXR and GST used in the GST pull down reaction. The position of the purified protein is marked (◄). The amount of full length GST-Cft1-$H_6$ is significantly less in comparison to GST-FXR or GST. Bottom Panels: GST-Cft1-$H_6$, GST-FXR or GST alone bound to glutathione beads were incubated with [$^{35}$S]-methionine labeled in vitro translated Aplysia CPEB. $\frac{1}{5}^{th}$ of the lysate used for binding reaction is loaded as input. The [$^{35}$S]-methionine labeled Aplysia CPEB binds specifically to the GST-Cft1, not to the other RNA binding protein such as FXR or to GST alone.
Figure 9D:
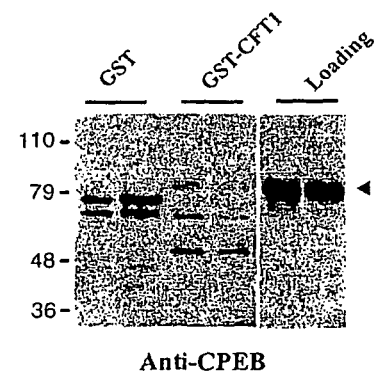
FIG. 9D: Total cell extracts prepared from Aplysia pleural ganglia were incubated with either GST-Cft1-$H_6$ or GST alone and the glutathione bead bound material was blotted with anti Aplysia CPEB antibodies. The position of Aplysia CPEB is marked with (◄). The right panel shows $\frac{1}{10}^{th}$ of the total Aplysia CPEB used in the binding reaction. The bands around 70 kd in GST lanes are cross-reacting polypeptides.

This 78 nucleotide fragment was fused to the 3' end of β-galactosidase mRNA, producing the fusion protein β-gal-CPE. As shown in FIG. 9B, when β-gal-CPE was expressed from a single-copy plasmid under a constitutive promoter, colonies remained white on plates containing X-Gal (only 1/5376 blue colonies, or about 0.02% after 2 days). In contrast, when the cyclin B1 78 nt fragment was replaced with other sequences of varying lengths and nucleotide composition the transformants turned blue within 10-12 hrs (FIG. 9). Although the constructs produced different levels of β-galactosidase activity, they produced the same levels of RNA at steady state. The poor translation of the β-gal-CPE mRNA indicates that the 78 nucleotides of cyclin B1 mRNA makes the β-gal mRNA translationally dormant. This poor translation could be due to the binding of some endogenous yeast protein to the U rich sequence of cyclin B1 UTR or formation of stable secondary structures at the 3' end of the mRNA.

When cells containing β-gal-CPE mRNA were co-transformed with a plasmid comprising ApCPEB, 21% of the colonies turned blue in 2 days (228/1091). Co-transformation with an empty plasmid or one expressing the unrelated yeast protein Ade1p failed to produce any blue colonies (in 2340 or 2136 transformants, respectively), indicating that activation of the β-gal-CPE fusion protein was dependent on ApCPEB. Even a plasmid expressing the neuronal isoform of another RNA-binding protein, Staufen, very rarely gave rise to blue colonies (3 in 2821). Moreover, when two conserved residues in the Zn finger domain of CPEB known to be important for RNA binding, Cys664 and His672, were mutated to alanine, the number of blue colonies was drastically reduced (6/1478 transformants, or about 4%).

Next we asked if *Aplysia* CPEB interacts with the yeast polyadenylation machinery, and whether the activated mRNA has longer polyA tail. We used a recombinant GST-tagged Cft1, the yeast homologue of mammalian cleavage and polyadenylation specificity factor, CPSF160. This protein specifically interacted with in vitro translated $^{35}$S-methionine labeled *Aplysia* CPEB. However, we failed to detect any significant change in the polyA tail length of β-gal mRNA. The CPEB dependent activation of β-gal mRNA therefore most likely results from the binding of the *Aplysia* CPEB to the CPE and recruitment of the CPSF complex. Irrespective of its detailed mechanism of activation the assay, in principle, recapitulates the activity of CPEB i.e., selective translation of mRNA carrying a CPE.

Figure 10A:
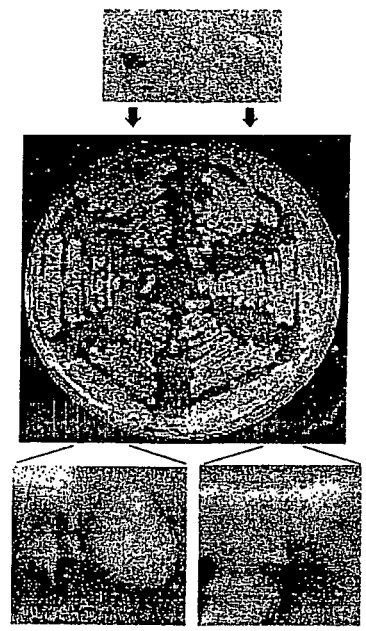
FIG. 10A: Full length ApCPEB can exist in two functionally distinct states. Top panel, representative blue and white cells expressing ApCPEB and β-gal-CPE; middle panel, maintenance of the blue and white phenotype upon restreaking; bottom panel, spontaneous conversion of blue and white cells.
Figure 10B:
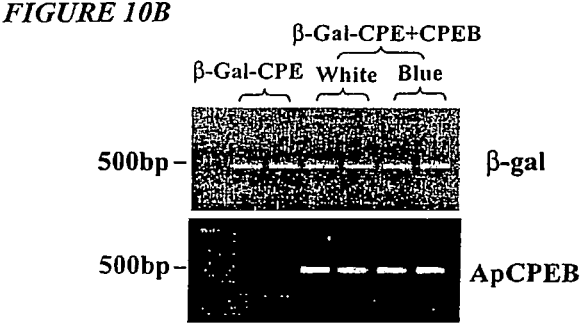
FIG. 10B: A similar amount of β-galactosidase mRNA and ApCPEB mRNA is present in both blue and white cells. Total RNA was isolated from blue and white cells and 3 ug of RNA was amplified in an RT-PCR reaction. Top panel, β-galactosidase mRNA; bottom panel, ApCPEB mRNA.
Figure 11A:
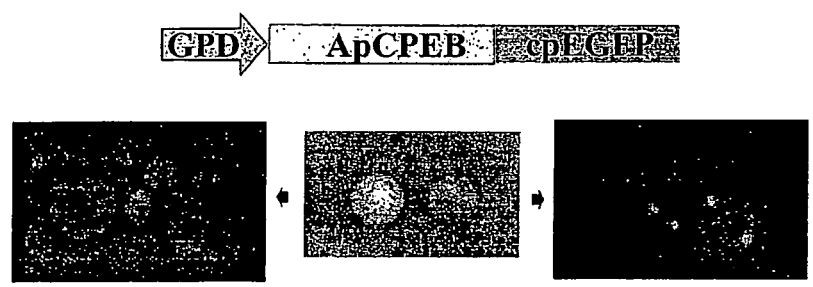
FIG. 11A: Two physical states of the Aplysia CPEB protein and dominant non-Mendelian inheritance of the Blue phenotype. Top: schematic of ApCPEB circularly permutated EGFP (cpEGFP) fusion construct. The GFP fluorescence of blue and white cells is shown below.
Figure 11B:
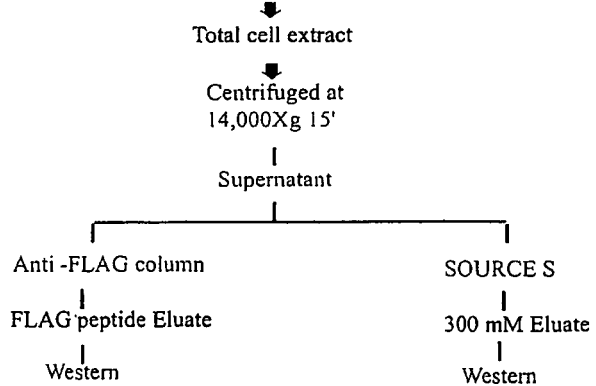
FIG. 11B: Schematic of the experiments. Blue or white transformants were grown in 1 liter of selective media (-Leu-Ura) to log phase and cell extracts were prepared using glass beads. The total cell lysates were centrifuged at 14,000×g to clarify the extract. Approximately 1 mg of total protein was loaded into an anti-FLAG antibody column and eluted with FLAG peptide. For purification through SOURCE S cation exchanger, approximately 100 mg of total protein was loaded into the column and washed with a buffer containing 150 mM NaCl. *Aplysia* CPEB came out of the column in 300 mM NaCl. The 300 mM fractions were pooled, concentrated and used in the protease assay.

As with the natural yeast prions and the CPEBQ-GR$^{526}$ fusion protein, the activity states of established colonies expressing full-length CPEB were heritable, but metastable. On re-plating the majority of blue colonies gave rise to blue colonies (FIG. 10A, middle). However, occasionally blue colonies would give rise to white (FIG. 11A, bottom). These, too, propagated faithfully but occasionally gave rise again to blue colonies. Notably, the expression of β-gal-CPE mRNA and of both CPEB protein and mRNA were the same in blue and white colonies (FIG. 10B and data not shown). Moreover, the specific activity of the β-galactosidase in white CPEB cells was low but detectable, similar to that of cells expressing β-gal-CPE mRNA alone (data not shown). Thus, white cells made a β-galactosidase mRNA that was capable of producing active enzyme but the mRNA was not efficiently translated.

Distinct ApCPEB Functional States Correlate with Distinct Physical States

The ability of the yeast prions to exist in distinct physical states is commonly detected by direct visualization of green fluorescent protein (GFP) fusions (Patino et al., 1996; Sondheimer and Lindquist, 2000). In order to visualize the physical state of the *Aplysia* CPEB in blue and white cells we fused *Aplysia* CPEB to a variant of GFP (cpEGFP) (FIG. 11A). The fusion of the cpEGFP to the C-terminal end of *Aplysia* CPEB did not interfere with the proteins activity and the fusion protein gave rise to blue cells when yeast cells were co-transformed with the β-gal-CPE construct. When we analyzed the fluorescence of cpEGFP in white cells we noticed a diffused fluorescence of GFP as has been observed for GFP alone (FIG. 11A). In contrast in blue cells there was a striking coalescence of the GFP fluorescence. Moreover, the soluble and aggregated states of the fusion protein seem to be heritable, because the vast majority of the daughter cells have the same soluble or aggregated state as the mother.

Figure 11C:
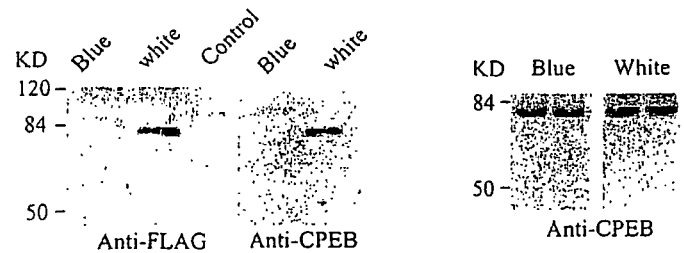
FIG. 11C: Left panel: ApCPEB protein was detected by Western blotting using ⅕th of the FLAG column eluate and either anti-FLAG antibodies or with anti ApCPEB antibodies.

By immunoblotting similar levels of CPEB were detected in total proteins from blue and white colonies, but the signals were too faint for further analysis. To enrich the protein for other assays, we introduced a 3×FLAG tag at its C-terminal end. Tagged CPEB behaved like untagged CPEB in vivo. Surprisingly, when lysates were passed over an anti-FLAG affinity column, the CPEB-FLAG protein from white colonies but not blue colonies was retained on the column (FIG. 11C). Similar results were obtained in the presence of 1% Triton™ X-100, a detergent that disrupts many protein complexes, but allows efficient binding of anti-FLAG antibody to FLAG tagged proteins. In contrast when FLAG-tagged CPEB was purified by cation-exchange chromatography, similar quantities were obtained from both cell types (FIG. 11D). Thus, the CPEB protein in blue cells, but not in white cells is in a physical state that produces small aggregates and limits the accessibility of the C-terminal region of the protein to the antibody. Whether this is solely due to the conformational state of CBEB itself or binding of other factors is unclear. In either case the heritable differences in the activity states of full length CPEB in blue and white cells are associated with distinct physical state of the protein.

The Active Form of ApCPEB Protein is the Transmissible State

Surprisingly, when blue W303a cells were mated to white W303α cells diploids were blue on X-gal plates. Thus, unlike CPEBQ-GR, the active form of ApCPEB is dominant. This might indicate that the ApCPEB protein is not capable of producing a transmissible prion-like state or that, unlike CPEBQ-GR and other well characterized yeast prions, it is the active form of the protein that is the prion-like state. Though unexpected, this would be in keeping with the observation that it is the active form of ApCPEB-FLAG (i.e. the protein of blue cells) in which accessibility of the C-terminal domain of the protein is altered, and it is in the blue cells that the protein forms small aggregates.

Figure 12A:
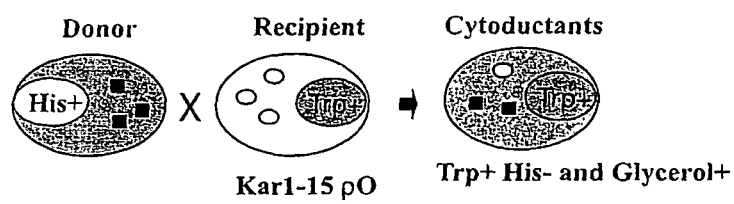
FIG. 12A: Schematic representation of cytoduction. W303 cells (mating type α) were transformed with ApCPEB and β-galactosidase-CPE and blue cells were selected. These cells were cytoduced to A3464 (mating type a) white cells and cytoductants were selected on media lacking histidine and had glycerol as the sole carbon source. This selected against W303α, which was his3Δ-200 and the noncytoduced A3464, which lacked mitochondrial DNA and unable to grow in glycerol. The haploid cytoductants were plated on 2% X-Gal.
Figure 12B:
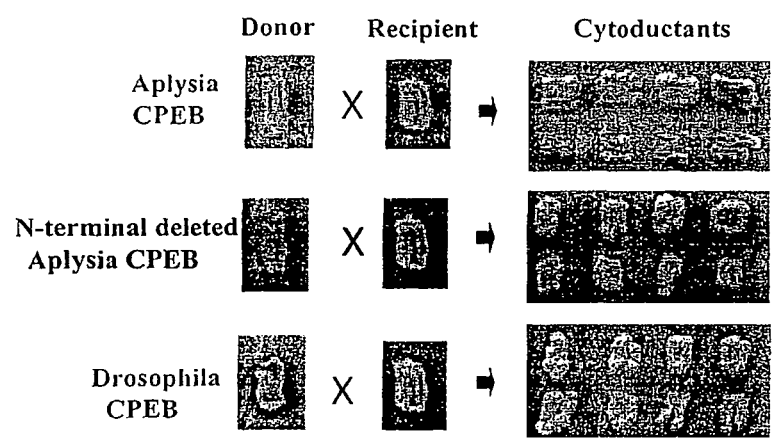
FIG. 12B: Representative blue and white cells and eight of the resultant haploid cytoduced cells in X-gal plate arc-shown-below-the-schematic.

Cytoduction provides a more rigorous test of the prion state than dominance in simple matings and has previously been used to establish the prion properties of yeast [UER3], [PSI], and [RNQ] (Wickner, R. B. 1994; Patino et al., 1996; Sondheimer and Lindquist, 2000). The yeast karyogamy deficient strain A3464 (KarΔ1-15) MATa can undergo normal conjugation with MATα strains, but is unable to fuse its nucleus with that of its mating partners. As a result, organelles are mixed and cytoplasmic proteins from the two cells come in contact with each other, but haploid progeny that bud from the mating pair contain nuclear information from just one of the parents. We used blue W303α (H+) cells expressing ApCPEB and β-gal-CPE mRNA as the donors of cytoplasmic material and white A3464 (Trp+) cells expressing ApCPEB-cpEGFP and β-gal-CPE mRNA as the recipients (FIG. 12A). To ensure cytoplasmic transfer from donor cells, the cytoplasm of the A3464 cells was marked with a petite mitochondrial mutation (p0). A3464 cells are unable to grow in a non-fermentable carbon source, such as glycerol unless they received wild-type mitochondria from the donor cytoplasm. Following cytoduction, haploid progeny were selected that had A3464 nuclear markers but had received cytoplasmic material from the donor (FIG. 12B). When plated onto X-GAL plates most of these haploid cells turned blue (14 out of 19 cytoduced cells turned blue). To control for the unlikely possibility that the small quantity of β-galactosidase enzyme transferred in the cytoduction would be sufficient to turn colonies blue, we cytoduced unrelated blue cells expressing β-galactosidase to the same white recipients. The cytoduced haploid cells of this mating either did not turn blue at all or exhibited only the light blue color seen in cells translating β-gal-CPE mRNA at low efficiency (data not shown).

The Prion-Like Determinant of CPEB Promotes and Maintains the Active State of the Protein One explanation for the difference between GF fusion protein (in which the prion state is inactive) and full length CPEB (in which the prion state is active) is that the prion domain of CPEB is capable of undergoing the same type of self-perpetuating change in state that yeast prion proteins undergo but that this has a different biological consequence in its natural protein context. If the C-terminal region of CPEB has a relatively weak or unstable capacity to activate CPE-containing mRNAs on its own, the self-perpetuating change in state conferred by the N-terminal domain might be employed to stabilize it in the active state.

To test this possibility, the N-terminal 200 amino acids of ApCPEB was deleted and the truncated protein was co-expressed with β-gal-CPE mRNA. Compared to full length CPEB, fewer of the initial transformants turned blue after 2 days (22% blue colonies were obtained with the full length protein; 8% with the N-terminal deletion, 58 in 680 transformants).

To further investigate the role of the N-terminal domain we analyzed the rate of interconversion between the blue and white colonies expressing the full-length CPEB or the N-terminal deletion. Starting with established white transformants, cells expressing full length CPEB gave rise to blue colonies at a frequency of 0.4%. Cells expressing N-terminally truncated CPEB gave rise to blue colonies much less frequently (0.046%). Starting with established blue colonies, full length CPEB gave rise to white colonies at a frequency of 0.55% (29 white colonies vs 5252 blue colonies). N-terminally deleted CPEB gave rise to white colonies much more frequently (10.2%; 584 white colonies vs 5725 blue colonies). Moreover, when we fused an N-terminally truncated CPEB as donor in our cytoduction assay, it failed to confer the blue phenotype into the full length protein. Thus, even without the N-terminal domain, *Aplysia* CPEB can activate an mRNA containing CPEs and can assume alternative active states. However, the N-terminal domain increases the rate at which CPEB assumes the active heritable state and, once active, the N-terminal domain helps to maintain the protein in the active state and to transmit this state to the CPEB protein.

Hsp104 Overexpression Effects the Propagation of the Blue State

The propagation of most yeast prions depends on the amount and activity of the heat shock protein family members. HSP104 has the strongest effects: overexpression or deletion of the Hsp104 or Hsp70 family members eliminates the prion properties in most cases. To investigate whether the *Aplysia* CPEB prion-like properties were susceptible to the level of yeast heat shock proteins, we expressed Hsp104 from a multicopy plasmid. Blue cells obtained from full length *Aplysia* CPEB (FIG. 13A) turned white upon overexpression of Hsp104 (FIG. 13B). Hsp104 deletion had a very modest effect (FIG. 13C). The number of cells turning blue after the initial transformation or its maintenance on replating was similar to that of wild type cells. However, Hsp104 deletion had a significant affect on the N-terminally truncated CPEB. First, the number of initial transformants that turned blue was reduced by almost 50% (4% of the transformants turned blue compared to 8% under wild type background). Second, upon replating these blue cells could not propagate the blue phenotype stably. The effects of Hsp104 on the propagation of CPEB activity states are complex, but not unprecedented. Changes in Hsp104 expression can have different effects on even closely related prions and are influenced by sequences outside of the prion-determining region itself. The fact that Hsp104 (a conformation-remodeling factor of the AAA+ family) strongly influences the activity states of the CPEB protein supports the idea that these activity states are determined by changes in CPEB conformation.

The data presented here demonstrate that *Aplysia* CPEB has properties consistent with it being a prion-like protein. As in the case with other well-characterized prion determinants in yeast the N-terminal domain of *Aplysia* CPEB is modular and transferable. When fused to GR it produces distinct, heritable, functional states that are associated with distinct physical states; the prion state is inactive and this state is readily transmitted to cells with active protein in a dominant, heritable manner.

As is the case with conventional prions, the full length *Aplysia* CPEB also has a self-perpetuating epigenetic state that is associated with a distinct physical state. However, the full length CPEB differs from other yeast prions in a number of features. First, in the yeast prions characterized to date, the self-perpetuating state is a biochemically inactive state. By contrast, the dominant self-perpetuating state of CPEB is an active state. This is not completely unprecedented; the dominant self-perpetuating form of the fungal prion protein HetS is associated with a genetic gain of function although the biochemical function of [HetS] is still unknown (Coustou et al 1997). Our assay also suggests that in its active state the protein either forms small aggregates or multimers. How could a multimeric form of the protein be active? One possibility is that in the multimeric state the protein either retains or acquires certain biochemical activities, e.g., an ability to bind RNA or other proteins. Since we have failed to detect any post translation modification of the *Aplysia* CPEB in vivo, this raises the possibility that conformational changes induced by some other mechanism (such as prion-like conversion) might confer the altered activity. As is true for other prions, we do not as yet know if the change in state is self-autonomous or requires other factors. In any case, once the active state we have described is achieved it is self-perpetuating and transmissible.

Although we lack direct evidence in neurons we speculate that CPEB has at least two conformational states: one is inactive or acts as a repressor (perhaps monomeric); the other is active (perhaps multimeric). Based on these considerations we propose a model for CPEB, which represents a variant of conventional prion mechanisms. This, new variant has features that are particularly relevant in the context of long-term memory storage. Long-term memory in both invertebrates and mice involves long-term synapse-specific modifications. In the invertebrate *Aplysia* the synapse-specific modifications are mediated by serotonin, a modulatory neurotransmitter released during learning. This long-term synapse-specific modification requires independent mechanisms for both spatial restriction (synapse specificity) and for persistence (duration).

We have shown previously that serotonin produces part of its local actions by increasing the amount of CPEB in a restricted synapse-specific way. If CPEB has prion-like properties in *Aplysia* this single molecule can achieve persistence as well as restriction. For example, in a naïve synapse the basal level of CPEB is low. Unlike conventional prions in this state the protein might be less active, inactive, or may even inhibit translation of certain CPE containing mRNAs. Indeed in *Xenopus* oocytes CPEB acts both as a translational repressor and as an activator for Cyclin B1 mRNA (deMoor and Richter 1998; Mendez et al. 2002). Since synaptic stimulation by serotonin leads to an increase in the neuronal CPEB, serotonin might (either itself or in concert with other signals) trigger conversion to the prion-like state. It is noteworthy that the transient increase in the protein level acts as general trigger for the conversion of all yeast prion proteins to the prion state. The prion-state of neuronal CPEB, resulting from synaptic stimulation by serotonin might be more active, as well as have altered substrate specificity, or be devoid of the inhibitory function of the basal state. Once the prion state is achieved in the activated synapse, dormant mRNAs that are made in the cell body and distributed globally to all synapse could be activated locally. The prion-like state would thereby contribute to the long-term maintenance of self-sustaining synapse-specific plastic change.

REFERENCES

Bailey, C. H. and Chen, M. Morphological aspects of synaptic plasticity in *Aplysia*. An anatomical substrate for long-term memory. Ann. N.Y. Acad. Sci. 627, 181-96 (1991);

Bally-Cuif, L. et al. Characterization of the zebrafish Orb/CPEB-related RNA binding protein and localization of maternal components in the zebrafish oocyte. Mech. Dev. 77, 31-47 (1998);

Barco, A. et al. Expression of constitutively active CREB protein facilitates the late phase of long-term potentiation by enhancing synaptic capture. Cell 108, 689-703 (2002);

Brittis, P. A. et al. Axonal protein synthesis provides a mechanism for localized regulation at an intermediate target. Cell 110, 223-35 (2002);

Casadio, A. et al. A transient, neuron-wide form of CREB-mediated long-term facilitation can be stabilized at specific synapses by local protein synthesis. Cell 99, 221-37 (1999);

Chang, J. S. et al. Functioning of the *Drosophila* orb gene in gurken mRNA localization and translation. Development 128, 3169-77 (2001);

Chernoff, Y. O. et al. Role of the chaperone protein Hsp104 in propagation of the yeast prion-like factor [psi+]. Science 268, 880-84 (1995);

Collinge, J. Prion diseases of humans and animals: their causes and molecular basis. Annu. Rev. Neurosci. 24, 519-50 (2001);

Coustou, V. et al. The protein product of the het-s heterokaryon incompatibility gene of the fungus Podospora anserina behaves as a prion analog. Proc. Natl. Acad. Sci. U.S.A. 94:9773-78 (1997);

Contractor, A. et al. Trans-synaptic Eph receptor-ephrin signaling in hippocampal mossy fiber LTP. Science 296, 1864-69 (2002);

Crist, C. G. et al. [PHI+], a novel Sup35-prion variant propagated with non-Gln/Asn oligopeptide repeats in the absence of the chaperone protein Hsp104. Genes Cells 8:603-18 (2003);

de Moor, C. H. and Richter, J. D. Cytoplasmic polyadenylation elements mediate masking and unmasking of cyclin B1 mRNA. EMBO J. 18, 2294-303 (1999);

DePace, A. H., Santoso, A., Hillner, P. & Weissman, J. S. A critical role for amino-terminal glutamine/asparagine repeats in the formation and propagation of a yeast prion. Cell 93, 1241-52 (1998);

DesGroseillers, L. et al. A novel actin cDNA is expressed in the neurons of *Aplysia* californica. Biochim. Biophys. Acta. 1217, 322-24 (1994);

Dichtl, B. et al. Yhh1p/Cft1p directly links poly(A) site recognition and RNA polymerase II transcription termination. Embo J. 21:4125-35 (2002);

Ferreira, P. C. et al. The elimination of the yeast [PSI+] prion by guanidine hydrochloride is the result of Hsp104 inactivation. Mol. Microbiol. 40:1357-69 (2001);

Fox, C. A. et al. Poly(A) addition during maturation of frog oocytes: distinct nuclear and cytoplasmic activities and regulation by the sequence UUUUUAU. Genes Dev. 3, 2151-62 (1989);

Frey, U. and Morris, R. G. Synaptic tagging and long-term potentiation. Nature 385, 533-36 (1997);

Gebauer, F. and Richter, J. D. Mouse cytoplasmic polyadenylylation element binding protein: an evolutionarily conserved protein that interacts with the cytoplasmic polyadenylylation elements of c-mos mRNA. Proc. Natl. Acad. Sci. U.S.A. 93, 14602-607 (1996);

Gingras, A. C. et al. Regulation of translation initiation by FRAP/mTOR. Genes Dev. 15, 807-26. (2001);

Glover, J. R. et al. Self-seeded fibers formed by Sup35, the protein determinant of [PSI+], a heritable prion-like factor of *S. cerevisiae*. Cell 89, 811-19 (1997);

Groisman, I. et al. Translational control of the embryonic cell cycle. Cell 109, 473-83 (2002);

Hake, L. E. and Richter, J. D. CPEB is a specificity factor that mediates cytoplasmic polyadenylation during *Xenopus* oocyte maturation. Cell 79, 617-27 (1994);

Hake, L. E. et al. Specificity of RNA binding by CPEB: requirement for RNA recognition motifs and a novel zinc finger. Mol. Cell. Biol. 18, 685-93 (1998);

Hegde, A. N. et al. Ubiquitin C-terminal hydrolase is an immediate-early gene essential for long-term facilitation in *Aplysia*. Cell 89, 115-26 (1997);

Henderson, J. T. et al. The receptor tyrosine kinase EphB2 regulates NMDA-dependent synaptic function. Neuron 32, 1041-56 (2001);

Huang, Y. S. et al. N-methyl-D-aspartate receptor signaling results in Aurora kinase-catalyzed CPEB phosphorylation and alpha CaMKII mRNA polyadenylation at synapses. EMBO J. 21, 2139-48 (2002);

Kelly, A. and Lynch, M. A. Long-term potentiation in dentate gyrus of the rat is inhibited by the phosphoinositide 3-kinase inhibitor, wortmannin. Neuropharmacology 39, 643-51 (2000);

Khan, A. et al. Serotonin activates S6 kinase in a rapamycin-sensitive manner in *Aplysia* synaptosomes. J. Neurosci. 21, 382-91 (2001);

Kim, C. H. and Lisman, J. E. A role of actin filament in synaptic transmission and long-term potentiation. J. Neurosci 19, 4314-24 (1999);

King, C. Y. et al. Prion-inducing domain 2-114 of yeast Sup35 protein transforms in vitro into amyloid-like filaments. Proc. Natl. Acad. Sci. U.S.A. 94, 6618-22 (1997);

Kushnirov, V. V. et al. Prion properties of the Sup35 protein of yeast *Pichia methanolica*. EMBO J. 19:324-31 (2000);

Li, L. and Lindquist, S. Creating a protein-based element of inheritance. Science 287, 661-64 (2000);

Liu, J. and Schwartz, J. H. The cytoplasmic polyadenylation element binding protein and polyadenylation of messenger RNA in *Aplysia* neurons. Brain Res. 959, 68-76 (2003);

Liu, Q. R. et al. A developmental gene (Tolloid/BMP-1) is regulated in *Aplysia* neurons by treatments that induce long-term sensitization. J. Neurosci. 17, 755-64 (1997);

Loreni, F. et al. Transcription inhibitors stimulate translation of 5' TOP mRNAs through activation of S6 kinase and the mTOR/FRAP signalling pathway. Eur. J. Biochem. 267, 6594-601 (2000);

Martin, K. C. et al. Synapse-specific, long-term facilitation of *Aplysia* sensory to motor synapses: a function for local protein synthesis in memory storage. Cell 91, 927-38 (1997);

Masison, D. C. and Wickner, R. B. Prion-inducing domain of yeast Ure2p and protease resistance of Ure2p in prion-containing cells. Science 270, 93-95 (1995);

McGrew, L. et al. Poly(A) elongation during *Xenopus* oocyte maturation is required for translational recruitment and is mediated by a short sequence element. Genes Dev. 3, 803-15 (1989);

Mendez, R. and Richter, J. D. Translational control by CPEB: a means to the end. Nat. Rev. Mol. Cell. Biol. 2, 521-29 (2001);

Mendez, R. et al. Phosphorylation of CPE binding factor by Eg2 regulates translation of c-mos mRNA. Nature 404, 302-07 (2000);

Mendez, R. et al. Differential mRNA translation and meiotic progression require Cdc2-mediated CPEB destruction. EMBO J. 21, 1833-44 (2002);

Mendez, R. et al. Phosphorylation of CPEB by Eg2 mediates the recruitment of CPSF into an active cytoplasmic polyadenylation complex. Mol. Cell. 6, 1253-59 (2000);

Michelitsch, M. D. and Weissman, J. S. A census of glutamine/asparagine-rich regions: implications for their conserved function and the prediction of novel prions. Proc. Natl. Acad. Sci. U.S.A. 97, 11910-15 (2000);

Montarolo, P. G. et al. A critical period for macromolecular synthesis in long-term heterosynaptic facilitation in *Aplysia*. Science 234, 1249-54 (1986);

Moriyama, H. et al. [URE3] prion propagation in *Saccharomyces cerevisiae*: requirement for chaperone Hsp104 and curing by overexpressed chaperone Ydj1p. Mol. Cell. Biol. 20:8916-22 (2000);

Newnam, G. P. et al. Antagonistic interactions between yeast chaperones Hsp104 and Hsp70 in prion curing. Mol. Cell. Biol. 19:1325-33 (1999);

Osherovich, L. Z. and Weissman, J. S. Multiple Gln/Asn-rich prion domains confer susceptibility to induction of the yeast [PSI(+)] prion. Cell 106, 183-94 (2001);

Patino, M. M. et al. Support for the prion hypothesis for inheritance of a phenotypic trait in yeast. Science 273, 622-26 (1996);

Paushkin, S. V. et al. In vitro propagation of the prion-like state of yeast Sup35 protein. Science 277, 381-83 (1997);

Prusiner, S. B. Prions. Proc. Natl. Acad. Sci. U.S.A. 95, 13363-83 (1998);

Raymond, C. R. et al. The phosphoinositide 3-kinase and p70 S6 kinase regulate long-term potentiation in hippocampal neurons. Neuroscience 109, 531-36 (2002);

Reverte, C. G. et al. XGef is a CPEB-interacting protein involved in *Xenopus* oocyte maturation. Dev. Biol. 255: 383-98 (2003);

Salles, F. J. and Strickland, S. Analysis of poly(A) tail lengths by PCR: the PAT assay. Methods Mol. Biol. 118, 441-48 (1999);

Sanna, P. P. et al. Phosphatidylinositol 3-kinase is required for the expression but not for the induction or the maintenance of long-term potentiation in the hippocampal CA1 region. J. Neurosci 22, 3359-65 (2002);

Schacher, S. et al. Expression and branch-specific export of mRNA are regulated by synapse formation and interaction with specific postsynaptic targets. J. Neurosci 19; 6338-47 (1999);

Schroeder, K. E. et al. Spatially regulated translation in embryos: asymmetric expression of maternal Wnt-11 along the dorsal-ventral axis in *Xenopus*. Dev. Biol. 214, 288-97 (1999);

Schwarze, S. R. and Dowdy, S. F. In vivo protein transduction: intracellular delivery of biologically active proteins, compounds and DNA. Trends Pharmacol. Sci. 21, 45-48 (2000);

Shatkin, A. J. and Manley, J. L. The ends of the affair: capping and polyadenylation. Nat. Struc. Biol. 7:838-42 (2000);

Sondheimer, N. and Lindquist, S. Rnq1: an epigenetic modifier of protein function in yeast. Mol. Cell. 5, 163-72 (2000);

Sparrer, H. E. et al. Evidence for the prion hypothesis: induction of the yeast [PSI+] factor by in vitro-converted Sup35 protein. Science 289, 595-99 (2000);

Stebbins-Boaz, B. et al. CPEB controls the cytoplasmic polyadenylation of cyclin, Cdk2 and c-mos mRNAs and is necessary for oocyte maturation in *Xenopus*. EMBO J. 15, 2582-92 (1996);

Stumpf, G. and Domdey, H. Dependence of yeast pre-mRNA 3'-end processing on CFT1: a sequence homolog of the mammalian AAUAAA binding factor. Science 274:1517-20 (1996);

Tan, L. et al. An autoregulatory feedback loop directs the localized expression of the *Drosophila* CPEB protein Orb in the developing oocyte. Development 128, 1159-69 (2001);

True, H. L. and Lindquist, S. L. A yeast prion provides a mechanism for genetic variation and phenotypic diversity. Nature 407, 477-83 (2000);

Tuite, M. F. Yeast prions and their prion-forming domain. Cell 100, 289-92 (2000);

Wickner, R. B. and Masison, D. C. Evidence for two prions in yeast: [URE3] and [PSI]. Curr. Top. Microbiol. Immunol. 207, 147-60 (1996);

Wickner, R. B. [URE3] as an altered URE2 protein: evidence for a prion analog in *Saccharomyces cerevisiae*. Science 264, 566-69 (1994);

Wu, L. et al. CPEB-mediated cytoplasmic polyadenylation and the regulation of experience-dependent translation of alpha-CaMKII mRNA at synapses. Neuron 21, 1129-39 (1998); and Yang, F. et al. PI-3 kinase and IP3 are both necessary and sufficient to mediate NT3-induced synaptic potentiation. Nat. Neurosci. 4, 19-28 (2001).

What is claimed is:

1. A method for determining whether an agent facilitates conversion of a neuron-specific isoform of cytoplasmic polyadenylation element binding (CPEB) protein from a non-prion form to a prion form comprising the steps of:
   (a) determining the amount of prion form in a population of the neuron-specific isoform of CPEB protein;
   (b) contacting the population of the neuron-specific isoform of CPEB protein with the agent;
   (c) after a suitable period of time, determining whether the amount of prion form in the contacted population of the neuron-specific isoform of CPEB protein is greater in the presence of the agent than in the absence of the agent; and
   (d) determining, when a greater amount of the prion form of the neuron-specific isoform of CPEB protein is present after step (c), that the agent facilitates the conversion of the neuron-specific isoform of CPEB protein from a non-prion form to a prion form.

2. The method of claim 1, wherein determining the amount of the prion form in a population of the neuron-specific isoform of CPEB protein comprises determining the susceptibility of the neuron-specific isoform of CPEB protein to protease digestion, wherein CPEB proteins that are not susceptible to protease digestion are determined to be in prion form.

3. The method of claim 1, wherein determining the amount of the prion form in a population of the neuron-specific isoform of CPEB protein comprises determining the amount of aggregate of the neuron-specific isoform of CPEB protein collected by centrifugation.

4. The method of claim 1, wherein the neuron-specific isoform of CPEB is ApCPEB, CG5735RA or KIAA0940.

5. A method for determining whether an agent facilitates conversion of a neuron-specific isoform of cytoplasmic polyadenylation element binding (CPEB) protein from a non-prion form to a prion form comprising the steps of:
   (a) determining the amount of prion form of the neuron-specific isoform of CPEB protein in a population of cells;
   (b) contacting the population of cells with the agent, each of which cells comprise the neuron-specific isoform of CPEB protein;
   (c) after a suitable period of time, determining whether the amount of the prion form of the neuron-specific isoform of CPEB protein in the contacted population of cells is greater in the presence of the agent than in the absence of the agent; and
   (d) determining, when a greater amount of the prion form of the neuron-specific isoform of CPEB protein is present after step (c), that the agent facilitates the conversion of the neuron-specific isoform of CPEB protein from a non-prion form to a prion form.

6. The method of claim 5, wherein determining the amount of the prion form of the neuron-specific isoform of CPEB protein comprises determining the susceptibility of the neuron-specific isoform of CPEB protein to protease digestion.

7. The method of claim 5, wherein determining the amount of the prion form of the neuron-specific isoform of CPEB protein comprises determining the amount of aggregate of the neuron-specific isoform of CPEB protein collected by centrifugation.

8. The method of claim 5, wherein the cell is a eukaryotic cell.

9. The method of claim 8, wherein the cell is a yeast cell.

10. The method of claim 9, wherein the yeast cell is an *S. cerevisiae* cell.

11. The method of claim 8, wherein the neuron-specific isoform of CPEB protein is endogenously expressed in the population of cells.

12. The method of claim 11, wherein the population of cells is obtained from central nervous system tissue.

13. The method of claim 12, wherein the population of cells is a population of neuronal cells.

14. The method of claim 13, wherein the population of cells is further contacted with a neurotransmitter prior to, concurrently with, or subsequent to contacting with the agent.

15. The method of claim 5, wherein the neuron-specific isoform of CPEB is ApCPEB, CG5735RA or KIAA0940.

* * * * *

SEQUENCE LISTING

```
<160> NUMBER OF SEQ ID NOS: 34

<210> SEQ ID NO 1
<211> LENGTH: 78
<212> TYPE: DNA
<213> ORGANISM: Saccharomyces cerevisiae

<400> SEQUENCE: 1
ggaattcggc accatgtgct tctgtaaata gtgtattgtg tttttaatgt tggactggtt      60
ggaataaagc tctagagc                                                   78

<210> SEQ ID NO 2
<211> LENGTH: 27
<212> TYPE: DNA
<213> ORGANISM: Artificial Sequence
<220> FEATURE:
<223> OTHER INFORMATION: Primer directed to Aplysia cDNA
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: s is g, or c
<220> FEATURE:
<221> NAME/KEY: misc_feature
<222> LOCATION: (15)..(15)
<223> OTHER INFORMATION: r is g, or a
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: h is a, or c, or t/u
<220> FEATURE:
<221> NAME/KEY: misc_feature
<222> LOCATION: (24)..(24)
<223> OTHER INFORMATION: n is a, c, g, or t

<400> SEQUENCE: 2
gcggaattcg tnsargtnat hccntgg                                         27

<210> SEQ ID NO 3
<211> LENGTH: 26
<212> TYPE: DNA
<213> ORGANISM: Artificial Sequence
<220> FEATURE:
<223> OTHER INFORMATION: Primer directed to Aplysia cDNA
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
```

```
<223> OTHER INFORMATION: s is g, or c
<220> FEATURE:
<221> NAME/KEY: misc_feature
<222> LOCATION: (24)..(24)
<223> OTHER INFORMATION: r is g, or a

<400> SEQUENCE: 3
gcgggatcct gntgccants ccarca                                          26

<210> SEQ ID NO 4
<211> LENGTH: 21
<212> TYPE: DNA
<213> ORGANISM: Artificial Sequence
<220> FEATURE:
<223> OTHER INFORMATION: Primer directed to Aplysia mRNA

<400> SEQUENCE: 4
cactgtcttg ttcgactcca g                                               21

<210> SEQ ID NO 5
<211> LENGTH: 20
<212> TYPE: DNA
<213> ORGANISM: Artificial Sequence
<220> FEATURE:
<223> OTHER INFORMATION: Primer directed to Aplysia mRNA

<400> SEQUENCE: 5
aacacatggt tactgtccgc                                                 20

<210> SEQ ID NO 6
<211> LENGTH: 24
<212> TYPE: DNA
<213> ORGANISM: Artificial Sequence
<220> FEATURE:
<223> OTHER INFORMATION: Primer directed to Aplysia mRNA

<400> SEQUENCE: 6
catgaaagcc gtgcaagctg catt                                            24

<210> SEQ ID NO 7
<211> LENGTH: 27
<212> TYPE: DNA
<213> ORGANISM: Artificial Sequence
<220> FEATURE:
<223> OTHER INFORMATION: Primer directed to Drosophila melanogaster mRNA
      and cDNA

<400> SEQUENCE: 7
cgggatccat gtacaacaaa tttgtta                                         27

<210> SEQ ID NO 8
<211> LENGTH: 26
<212> TYPE: DNA
<213> ORGANISM: Artificial Sequence
<220> FEATURE:
<223> OTHER INFORMATION: Primer directed to Drosophila melanogaster mRNA

<400> SEQUENCE: 8
tccccgcggc gatcctccgc ctcctc                                          26

<210> SEQ ID NO 9
<211> LENGTH: 21
<212> TYPE: DNA
<213> ORGANISM: Artificial Sequence
<220> FEATURE:
<223> OTHER INFORMATION: Primer directed to Drosophila melanogaster mRNA
```

<400> SEQUENCE: 9
atggactcgc tcaagttacc a                                      21

<210> SEQ ID NO 10
<211> LENGTH: 24
<212> TYPE: DNA
<213> ORGANISM: Artificial Sequence
<220> FEATURE:
<223> OTHER INFORMATION: Primer directed to Drosophila melanogaster mRNA

<400> SEQUENCE: 10
cgcgatgcct gattgattgt tgaa                                   24

<210> SEQ ID NO 11
<211> LENGTH: 24
<212> TYPE: DNA
<213> ORGANISM: Artificial Sequence
<220> FEATURE:
<223> OTHER INFORMATION: Primer directed to Drosophila melanogaster mRNA

<400> SEQUENCE: 11
tgtgcgttat tttatcgttt agtg                                   24

<210> SEQ ID NO 12
<211> LENGTH: 21
<212> TYPE: DNA
<213> ORGANISM: Artificial Sequence
<220> FEATURE:
<223> OTHER INFORMATION: Primer directed to Drosophila melanogaster mRNA

<400> SEQUENCE: 12
gacttcatcc gccaccagtc g                                      21

<210> SEQ ID NO 13
<211> LENGTH: 22
<212> TYPE: DNA
<213> ORGANISM: Artificial Sequence
<220> FEATURE:
<223> OTHER INFORMATION: Primer directed to Drosophila melanogaster mRNA

<400> SEQUENCE: 13
caccaggaac ttcttgaatc cg                                     22

<210> SEQ ID NO 14
<211> LENGTH: 35
<212> TYPE: DNA
<213> ORGANISM: Artificial Sequence
<220> FEATURE:
<223> OTHER INFORMATION: Primer directed to Drosophila melanogaster cDNA

<400> SEQUENCE: 14
ccctcgagaa gcttttaaca ccagcgaaag gggac                       35

<210> SEQ ID NO 15
<211> LENGTH: 28
<212> TYPE: DNA
<213> ORGANISM: Artificial Sequence
<220> FEATURE:
<223> OTHER INFORMATION: Primer directed to Drosophila melanogaster cDNA

<400> SEQUENCE: 15
cgggatccat gctggacagc aacaacag                               28

<210> SEQ ID NO 16
<211> LENGTH: 31

```
<212> TYPE: DNA
<213> ORGANISM: Artificial Sequence
<220> FEATURE:
<223> OTHER INFORMATION: Primer directed to Drosophila melanogaster cDNA

<400> SEQUENCE: 16
gactagtcta gaatagatta gcaaagaaat c                                    31

<210> SEQ ID NO 17
<211> LENGTH: 26
<212> TYPE: DNA
<213> ORGANISM: Artificial Sequence
<220> FEATURE:
<223> OTHER INFORMATION: Primer directed to Aplysia neuronal actin cDNA

<400> SEQUENCE: 17
gggaattcgt ctggagccac caacac                                          26

<210> SEQ ID NO 18
<211> LENGTH: 41
<212> TYPE: DNA
<213> ORGANISM: Artificial Sequence
<220> FEATURE:
<223> OTHER INFORMATION: Primer directed to Aplysia neuronal actin

<400> SEQUENCE: 18
cggatccatt tattaacatt gtataaaaaa tacagttgaa c                         41

<210> SEQ ID NO 19
<211> LENGTH: 41
<212> TYPE: DNA
<213> ORGANISM: Artificial Sequence
<220> FEATURE:
<223> OTHER INFORMATION: Primer directed to Aplysia neuronal actin

<400> SEQUENCE: 19
cggatccatt tattaacatt gtatgggaaa tacagttgaa c                         41

<210> SEQ ID NO 20
<211> LENGTH: 25
<212> TYPE: DNA
<213> ORGANISM: Artificial Sequence
<220> FEATURE:
<223> OTHER INFORMATION: Primer directed to Aplysia CPEB cDNA

<400> SEQUENCE: 20
cgggatccat gcaagccatg gccgt                                           25

<210> SEQ ID NO 21
<211> LENGTH: 24
<212> TYPE: DNA
<213> ORGANISM: Artificial Sequence
<220> FEATURE:
<223> OTHER INFORMATION: Primer directed to Aplysia CPEB cDNA

<400> SEQUENCE: 21
tccccgcggt ggaccaggcg tgta                                            24

<210> SEQ ID NO 22
<211> LENGTH: 17
<212> TYPE: PRT
<213> ORGANISM: Artificial Sequence
<220> FEATURE:
<223> OTHER INFORMATION: C-terminal peptide of CPEB (CPEB77)

<400> SEQUENCE: 22
```

Leu Cys Asn Ser His Gln Gly Asn Tyr Phe Cys Arg Asp Leu Leu Cys
1               5                   10                  15
Phe

<210> SEQ ID NO 23
<211> LENGTH: 30
<212> TYPE: DNA
<213> ORGANISM: Artificial Sequence
<220> FEATURE:
<223> OTHER INFORMATION: Primer directed to Aplysia RNA

<400> SEQUENCE: 23
gcgagctccg cggccgcgtt tttttttttt                              30

<210> SEQ ID NO 24
<211> LENGTH: 21
<212> TYPE: DNA
<213> ORGANISM: Artificial Sequence
<220> FEATURE:
<223> OTHER INFORMATION: Primer directed to Aplysia sensorin RNA

<400> SEQUENCE: 24
aacagaaaca gtctttcccc c                                       21

<210> SEQ ID NO 25
<211> LENGTH: 19
<212> TYPE: DNA
<213> ORGANISM: Artificial Sequence
<220> FEATURE:
<223> OTHER INFORMATION: Primer directed to Aplysia sensorin RNA

<400> SEQUENCE: 25
tcttgactca ccaactgcc                                          19

<210> SEQ ID NO 26
<211> LENGTH: 24
<212> TYPE: DNA
<213> ORGANISM: Artificial Sequence
<220> FEATURE:
<223> OTHER INFORMATION: Primer directed to Aplysia Bmp1 RNA

<400> SEQUENCE: 26
atctatcgcc tattattatc acca                                    24

<210> SEQ ID NO 27
<211> LENGTH: 20
<212> TYPE: DNA
<213> ORGANISM: Artificial Sequence
<220> FEATURE:
<223> OTHER INFORMATION: Primer directed to Aplysia Bmp1 RNA

<400> SEQUENCE: 27
atcccatgca tttgtttgtt                                         20

<210> SEQ ID NO 28
<211> LENGTH: 17
<212> TYPE: DNA
<213> ORGANISM: Artificial Sequence
<220> FEATURE:
<223> OTHER INFORMATION: Primer directed to Aplysia N-actin RNA

<400> SEQUENCE: 28
cccatccatt gtccaca                                            17

<210> SEQ ID NO 29

-continued

```
<211> LENGTH: 18
<212> TYPE: DNA
<213> ORGANISM: Artificial Sequence
<220> FEATURE:
<223> OTHER INFORMATION: Primer directed to Aplysia N-actin RNA

<400> SEQUENCE: 29
tttgagcatt ctggcttc                                                  18

<210> SEQ ID NO 30
<211> LENGTH: 28
<212> TYPE: DNA
<213> ORGANISM: Artificial Sequence
<220> FEATURE:
<223> OTHER INFORMATION: Antisense oilgo directed to Aplysia CPEB mRNA

<400> SEQUENCE: 30
aaacagagca ggtcccggca gaaatagt                                       28

<210> SEQ ID NO 31
<211> LENGTH: 160
<212> TYPE: PRT
<213> ORGANISM: Aplysia californica

<400> SEQUENCE: 31

Met Gln Ala Met Ala Val Ala Ser Gln Ser Pro Gln Thr Val Asp Gln
1               5                   10                  15

Ala Ile Ser Val Lys Thr Asp Tyr Glu Asp Asn Gln Glu His Ile
            20                  25                  30

Pro Ser Asn Phe Glu Ile Phe Arg Arg Ile Asn Ala Leu Leu Asp Asn
        35                  40                  45

Ser Leu Glu Ala Asn Asn Val Ser Cys Ser Gln Ser Gln Ser Gln Gln
    50                  55                  60

Gln Gln Gln Gln Thr Gln Gln Gln Gln Gln Gln Gln Gln Gln Gln
65                  70                  75                  80

Gln Gln Gln His Leu Gln Gln Val Gln Gln Gln Arg Leu Leu Lys Gln
                85                  90                  95

Gln Gln Gln Gln Ala Gln Arg Gln Gln Ile Gln Gln Gln Leu Leu Gln
            100                 105                 110

Gln Gln Gln Gln Lys Gln Gln Leu Gln Gln Gln Gln Gln Gln Asx Gln
        115                 120                 125

Leu Gln Gln Gln Gln Leu Gln Leu Gln Gln Leu Gln Gln Leu
    130                 135                 140

Gln His Ile Gln Lys Glu Pro Ser Ser His Thr Tyr Thr Pro Gly Pro
145                 150                 155                 160

<210> SEQ ID NO 32
<211> LENGTH: 4
<212> TYPE: PRT
<213> ORGANISM: Aplysia californica

<400> SEQUENCE: 32

Gln Gln Gln Leu
1

<210> SEQ ID NO 33
<211> LENGTH: 13
<212> TYPE: RNA
<213> ORGANISM: Artificial sequence
<220> FEATURE:
<223> OTHER INFORMATION: PolyA tail assay
```

-continued

```
<400> SEQUENCE: 33
aaaaaaaaaa aaa                                                      13

<210> SEQ ID NO 34
<211> LENGTH: 10
<212> TYPE: RNA
<213> ORGANISM: Artificial sequence
<220> FEATURE:
<223> OTHER INFORMATION: PolyA tail assay

<400> SEQUENCE: 34
aaaaaaaaaa                                                          10
```